United States Patent
Thatcher et al.

[11] Patent Number: 5,981,735
[45] Date of Patent: Nov. 9, 1999

[54] METHOD OF PLASMID DNA PRODUCTION AND PURIFICATION

[75] Inventors: David R. Thatcher, Macclesfield; Anthony Hitchcock, Wistaston; Julian A.J. Hanak, Macclesfield; Diane L. Varley, Willaston, all of United Kingdom

[73] Assignee: Cobra Therapeutics Limited, Staffordshire, United Kingdom

[21] Appl. No.: 08/798,825

[22] Filed: Feb. 12, 1997

Related U.S. Application Data

[60] Provisional application No. 60/012,736, Mar. 4, 1996, abandoned.

[30] Foreign Application Priority Data

Feb. 12, 1996 [GB] United Kingdom ................... 9602825

[51] Int. Cl.$^6$ ............................ A61K 35/00; C07H 21/00; C07H 23/00; A23J 1/00
[52] U.S. Cl. ........................ 536/25.4; 424/124; 435/384; 435/404; 536/26.52; 536/26.43; 71/8; 530/417
[58] Field of Search ................... 536/25.4, 26.42, 536/26.43; 424/124; 530/417; 435/384, 404; 71/8

[56] References Cited

FOREIGN PATENT DOCUMENTS

| | | | |
|---|---|---|---|
| WO 91/10721 | 7/1991 | WIPO ............................... | C12M 1/36 |
| WO 95/21177 | 8/1995 | WIPO ............................... | C07H 1/08 |
| WO 95/21179 | 8/1995 | WIPO ............................... | C07H 1/08 |
| WO 95/21250 | 8/1995 | WIPO ............................... | C12N 15/10 |
| WO 96/02658 | 2/1996 | WIPO ............................... | C12P 19/34 |
| WO 96/36706 | 11/1996 | WIPO ............................... | C12N 15/10 |

OTHER PUBLICATIONS

Birnboim, 1983, A rapid alkaline extraction method for the isolation of plasmid DNA, *Methods Enzymol.* 100:243–255.
Birnboim and Doly, 1979, A rapid alkaline extraction procedure for screening recombinant plasmid DNA, *Nucleic Acids Res.* 7: 1513–1523.

Blair et al., 1972, Isolation of supercoiled colicinogenic factor $E_1$ DNA sensitive to ribonuclease and alkali, *Proc. Natl. Acad. Sci. U.S.A.* 69: 2518–2522.

Clewell and Helinski, 1972, Effect of growth conditions on the formation of the relaxation complex of supercoiled ColE1 deoxyribonucleic acid and protein in *Escherichia coli*, *J. Bacteriol.* 110: 1135–1146.

Curless et al., 1991, Design and evaluation of a two–stage, cyclic, recombinant fermentation process, *Biotechnology and Bioengineering* 38: 1082–1090.

Fieschko, 1989, "Fermentation technology using recombinant microorganisms" in *Bio/Technology*, eds. H.J. Rhem and G. Reed. Weinheim: VCH Verlagsgesellschaft mbH 7b: 117–140.

Godson and Vapnek, 1973, A simple method of preparing large amounts of $\phi$X174 RF I supercoiled DNA, *Biochimica et Biophysica Acta* 299: 516–520.

Holmes and Quigley, 1981, A rapid boiling method for the preparation of bacterial plasmids, *Anal. Biochem.* 114: 193–197.

Schorr et al., 1995, Plasmid DNA for human gene therapy and DNA vaccines, *New York Academy of Sciences* 772: 271–273.

(List continued on next page.)

*Primary Examiner*—Ardin H. Marschel
*Assistant Examiner*—Joyce Tung
*Attorney, Agent, or Firm*—Woodcock Washburn Kurtz Mackiewicz & Norris LLP

[57] ABSTRACT

A scalable method for the production of highly purified plasmid DNA in Escherichia coli is described, which method includes growing plasmid-containing cells to a high biomass in exponential growth and lysing the cells by raising the pH of the culture to a carefully controlled pH value in which chromosomal DNA is denatured but plasmid DNA is reversibly renatured. The method has been developed for the production of pharmaceutical grade DNA for use in in vivo and ex vivo gene therapy.

36 Claims, 12 Drawing Sheets

OTHER PUBLICATIONS

Sambrook, J., E.F. Fritsch and T. Maniatis, eds., *Molecular Cloning. A Laboratory Manual.*, vol. 3, Appendix A, "Bacterial Media, Antibiotics and Bacteria Strains" (Terrific Broth; Tartoff and Hobbs, 1987), p. A.2, Cold Spring Harbor Laboratory Press, New York, 1989.

Camien, M.N. and R.C. Warner, 1986, Denaturation of covalently closed circular DNA, *J. Biol. Chem.*, 261(13): 6026–6033.

Sohail, A. et al., 1987, An improved method for isolation of covalently closed circular DNA ɸX174am3 phage, *Pakistan J. Zool.*, 19(4): 407–416.

AN 85–138896, XP002034003 & JP 60 075 283 A (Kikk KK, Kokuzei–Cho Chokan, Nikka Whisky KK, Takara Shuzo Co Ltd), Apr. 25, 1985, *Database WPI*, Week 8523, Derwent Publications, Ltd., London, GB.

European Patent Office International Search Report for PCT/GB 97/00386, Jul. 22, 1997.

← IRREVERSIBLY DENATURED PLASMID

← IRREVERSIBLY DENATURED PLASMID

IRREVERSIBLY DENATURED PLASMID

T gene = therapeutic gene
P/E = promoter/enhancer sequence
TT = Transcriptional terminator
S+P = splice and polyadenylation signals T gene = therapeutic gene
P/E = promoter/enhancer sequence
S+P = splice and polyadenylation signals T gene = therapeutic gene
P/E = promoter/enhancer sequence
S+P = splice and polyadenylation signals T gene = therapeutic gene
P/E = promoter/enhancer sequence
S+P = splice and polyadenylation signals

METHOD OF PLASMID DNA PRODUCTION AND PURIFICATION

This application is a continuation of U.S. provisional application Ser. No. 60/012,736, filed Mar. 4, 1996, and now abandoned.

FIELD OF THE INVENTION

This invention relates to the production of highly purified plasmid DNA, and in particular to production and isolation of pharmaceutical grade plasmid DNA for use in gene therapy.

BACKGROUND OF THE INVENTION

A variety of methods are available for isolating and purifying plasmid DNA. In general, these methods take advantage of the physical differences between chromosomal DNA and plasmid DNA. In terms of size, chromosomal DNA is larger than plasmid DNA. When cells are lysed, the larger chromosomal DNA becomes linearized and entangled in the cellular debris and may be separated from the cell lysate.

Prior art methods of isolating and purifying plasmid DNA include lysis by boiling (Holmes and Quigley, Anal. Biochem. 114, 193 (1981)), lysis with alkali (Birnboim and Doly, Nuc. Acids Res. 7, 1513 (1979)), and lysis with detergent (Godson and Vapnek, Biochem. Biophys. Acta 299, 516 (1973)). PCT publication no. 95/21250 discloses a method of isolating plasmid DNA using detergent in combination with alkali treatment. Prior art methods also use highly toxic chemicals to extract and isolate the plasmid DNA; such as ethidium bromide, cesium chloride, phenol, and chloroform. Moreover, these methods are most effective with smaller plasmids; e.g. plasmids less than approximately 8–10 kb. As plasmid size increases, plasmid DNA isolation becomes more difficult using the existing prior art methods.

In general, methods that employ alkali quickly add a standard amount of sodium hydroxide to the cellular suspension (Birnboim and Doly, supra). The pH of the resulting solution rises rapidly, in some cases, to over 13, which results in much degradation of the plasmid DNA. In addition, the concentration of the cells in suspension is dilute (i.e., of the order of an optical density (OD) of 1–3 units at a wavelength 600 nm for a 1 cm light path) to maximize recovery of plasmid DNA.

An object of the invention is to provide a method of preparing pharmaceutical grade DNA.

Another object of the invention is to provide a plasmid DNA preparation which is substantially free of bacterial host RNA.

Another object of the invention is to provide a plasmid DNA preparation which is substantially free of bacterial host protein.

Another object of the invention is to provide a plasmid DNA preparation which is substantially free of bacterial host chromosomal DNA.

Another object of the invention is to provide a plasmid DNA preparation which is substantially free of bacterial host endotoxins.

Another object of the invention is to provide a method of isolating and purifying relatively large plasmid DNAs.

Another object of the invention is to provide a scalable method of isolating large amounts of plasmid DNA in sufficiently pure form for use in gene therapy.

Another object of the invention is to maximize the yield of plasmid DNA from a host cell/plasmid DNA combination.

SUMMARY OF THE INVENTION

The invention is based on the discovery of a method for producing and isolating highly purified plasmid DNA. The plasmid DNA produced and isolated by the method of the invention contains very low levels of contaminating chromosomal DNA, RNA, protein, and endotoxins. The plasmid DNA produced according to the invention is of sufficient purity for use in vivo or ex vivo gene therapy.

Thus, the invention encompasses a process for producing and isolating highly purified plasmid DNA that includes the step of alkaline lysis in which the pH of the solution is monitored and raised in a controlled manner such that it does not rise above a predetermined pH value which is equal to 0.1 pH units below the irreversible alkaline denaturation value of the plasmid DNA.

Preferably, the predetermined pH value is equal to 0.2 pH units below the irreversible alkaline denaturation value of the plasmid DNA which is being isolated.

The predetermined pH value is within the range of 8.0 to 14.0 and is preferably within the range of about 11.0 to 13.1 and most preferably about 12.1 to 12.9.

The controlled rise in pH according to the method of the invention results in exceedingly low degradation of plasmid DNA, and thus permits higher yield of plasmid DNA.

As used herein, the terms "denature", "denatured DNA" and "denaturation" are defined as conformations of DNA in which the hydrogen bonds between strands of double stranded DNA are ruptured. The term "irreversible alkaline denaturation value" is defined as the pH value at which no more than about 50% of the alkaline denatured plasmid DNA fails to renature as determined by standard agarose gel electrophoresis. Determination of the irreversible alkaline denaturation value is described hereinbelow.

According to the invention, the alkaline lysis step is performed on cells harvested from a fermentation which has been grown to a biomass of cells that have not yet reached stationary phase, and are thus in exponential growth, about 2–10 g dry weight/liter.

In a preferred embodiment, the alkaline lysis step is performed on cells harvested from a fermentation which has been grown to a high biomass of cells that have not yet reached stationary phase and are thus in exponential growth.

As used herein, a "high biomass" or "high density" is defined as a cellular concentration of approximately 10–200 g dry weight per liter, and preferably 12–60 g dry weight per liter. As used herein, the term "exponential growth" refers to that portion of the cellular growth cycle between the lag phase and the stationary phase when cells are doubling at a logarithmic rate.

The term "exponential growth" is also meant to encompass the late lag phase (i.e., the early stationary phase) which occurs between the logarithmic growth phase and stationary phase, when the cell growth rate is slowing, and therefor encompasses an extended exponential growth phase. Therefore, "stationary phase" refers to horizontal growth, i.e., when the cells have essentially stopped dividing and have reached a quiescent stage with respect to cell doubling. According to the invention, the combination of controlled pH increase and lysis at high cell density from cells harvested during exponential growth produces a high yield of intact and highly pure plasmid DNA from a single batch of cells.

The invention also encompasses a method for determining the optimum lysis conditions for lysing host cells containing plasmid DNA, comprising the steps of a) growing a culture of bacterial host cells to a cell density within the range of about 12 g to about 60 g per liter dry weight units; b) lysing the bacterial cells during exponential growth at a pH of said culture sufficient to cause cell lysis and to cause denaturation of no greater than 50% of plasmid DNA contained in said cells; and c) selecting a pH value for optimum lysis conditions which is about 0.1 pH units below the pH of step b).

Preferably, the lysing step b) is performed at a pH sufficient to cause denaturation of no greater than 90–95% of plasmid DNA, and the pH selected in step c) is about 0.17–2.0 pH units below step b) pH.

Determining an optimum lysis pH or an optimum sodium hydroxide concentration for cell lysis according to the invention permits a longer time period during which cell lysis may occur, which in turn allows for a) destruction of larger amounts of undesirable endotoxin which may be present in the plasmid DNA preparation, b) denaturation of larger amounts of chromosomal DNA, and c) precipitation of larger amounts of chromosomal DNA, without concomitant loss of plasmid DNA in terms of quantity or loss of high quality plasmid DNA produced according to the invention.

The invention also thus encompasses a fermentation process which maximizes yield of plasmid DNAs from large scale cultures of transformed host cells. The fermentation process includes controlling the growth rate such that the supply of metabolites essential for growth is adequate to permit growth to a high biomass, but is not in excess so as to inhibit such growth. It is critical to this aspect of the invention that growth is not reduced by supplying inhibitory concentrations of metabolites and catabolites. However, it is also critical that components necessary for plasmid DNA production, such as nucleotides or nucleotide precursors, are not limiting during the fermentation process.

Another aspect of the invention is that plasmid DNA yield and quality is not reduced by insufficient concentrations of metabolites and nucleic acid precursors. Therefore, in another aspect the invention encompasses providing a culture growth medium having excess quantities of metabolites and nucleic acid precursors during the fermentation process; that is, concentrations in excess of those used in the prior art for the production of plasmid DNA in large scale fermentation.

In a preferred embodiment, the quantity of yeast extract in the batch medium is about 20 gm/liter, a 4-fold increase over conventional concentrations of yeast extract. In another preferred embodiment, the medium is supplemented with a source of organic nitrogen. Preferably, organic nitrogen is added to the culture medium in the form of ammonium salts such as ammonium sulfate or ammonium nitrate, at about 5 gm/liter or 10 gm/liter, or ammonium phosphate at 3 gm/liter, 5 gm/liter or 10 gm/liter.

The invention further encompasses a method of producing and isolating highly purified plasmid DNA that is essentially free of contaminants and thus is pharmaceutical grade DNA.

A plasmid DNA preparation isolated according to the methods of the invention may be subject to purification steps including ion exchange chromatography which may include both fluidized bed ion exchange chromatography and axial and/or radial high resolution anion exchange chromatography, and further may include gel permeation chromatography.

These methods thus include the alkaline lysis step described herein in combination with subsequent ion exchange chromatography and gel permeation chromatography steps.

Alternatively, in a preferred embodiment of the invention, it has been discovered that high resolution anion exchange chromatography is not necessary to arrive at highly pure plasmid DNA. Therefore, the alkaline lysis step may be combined with a plasmid DNA isolation step which includes only fluidized bed ion exchange chromatography and does not include additional axial or radial high resolution anion exchange chromatgraphy. Therefore, in this method of the invention, the ion exchange chromatography step consists essentially of fluidized bed ion exchange chromatography. In this aspect of the invention, the method may further consist essentially of gel permeation chromatography.

Ion exchange chromatography and gel permeation chromatography facilitate rapid and large scale isolation of plasmid DNA, and allow one of skill in the art to avoid use of highly toxic chemicals such as ethidium bromide, chloroform, and phenol, at least traces of which often appear in the final preparation. According to the invention, the gel permeation chromatography step in the process also provides for isolation of the plasmid DNA in a pharmaceutically acceptable solution.

The terms "essentially free", and "highly purified" are defined as about 95% and preferably greater than 98.99% pure or free of contaminants, or possessing less than 5%, and preferably less than 1–2% contaminants. "Pharmaceutical grade DNA" is defined herein as a DNA preparation that contains no more than about 5%, and preferably no more than about 1–2% of cellular components, such as cell membranes, chromosomal DNA (preferably <1%), RNA (preferably <0.2%), protein (preferably <1%) and other cell derived contaminants. Pharmaceutical grade DNA should contain no more than 100 EU/mg endotoxins, and is preferably predominant circular in form.

The invention also encompasses isolation of relatively large plasmid DNAs, i.e., in the size range of from approximately 5 kb to approximately 50 kb, preferably 15 kb to 50 kb, which DNA includes a vector backbone of approximately 3 kb, a therapeutic gene and associated regulatory sequences. Preferably, the vector backbone used in the method of the invention specifies a high copy number, a polylinker for insertion of a therapeutic gene, a gene encoding a selectable marker, e.g., the tetracycline or kanamycin resistance gene, and is physically small and stable. The approximate 3 kb vector backbone of the plasmid advantageously permits inserts of large fragments of mammalian, other eukaryotic, prokaryotic or viral DNA, and the resulting large plasmid may be purified and used in vivo or ex vivo human gene therapy.

Methods of the invention described herein for preparing pharmaceutical grade plasmid DNA that is highly pure and intact are advantageous over prior art methods in that the methods described herein are scalable and thus amenable to scale-up to large-scale manufacture. Such methods do not depend upon purification techniques which utilize toxic organic extractants or animal-derived proteins such as lysozyme and proteinases. Nor do methods of the invention require the use of mutagenic reagents such as ethidium bromide for plasmid DNA isolation. Nor do the methods of the invention require the use of large volumes of flammable solvents such as ethanol or propan-2-ol.

BRIEF DESCRIPTION OF THE DRAWINGS

The invention will be more fully understood from the following detailed description taken in conjunction with the accompanying drawings in which.

DESCRIPTION OF THE INVENTION

Figure 1:
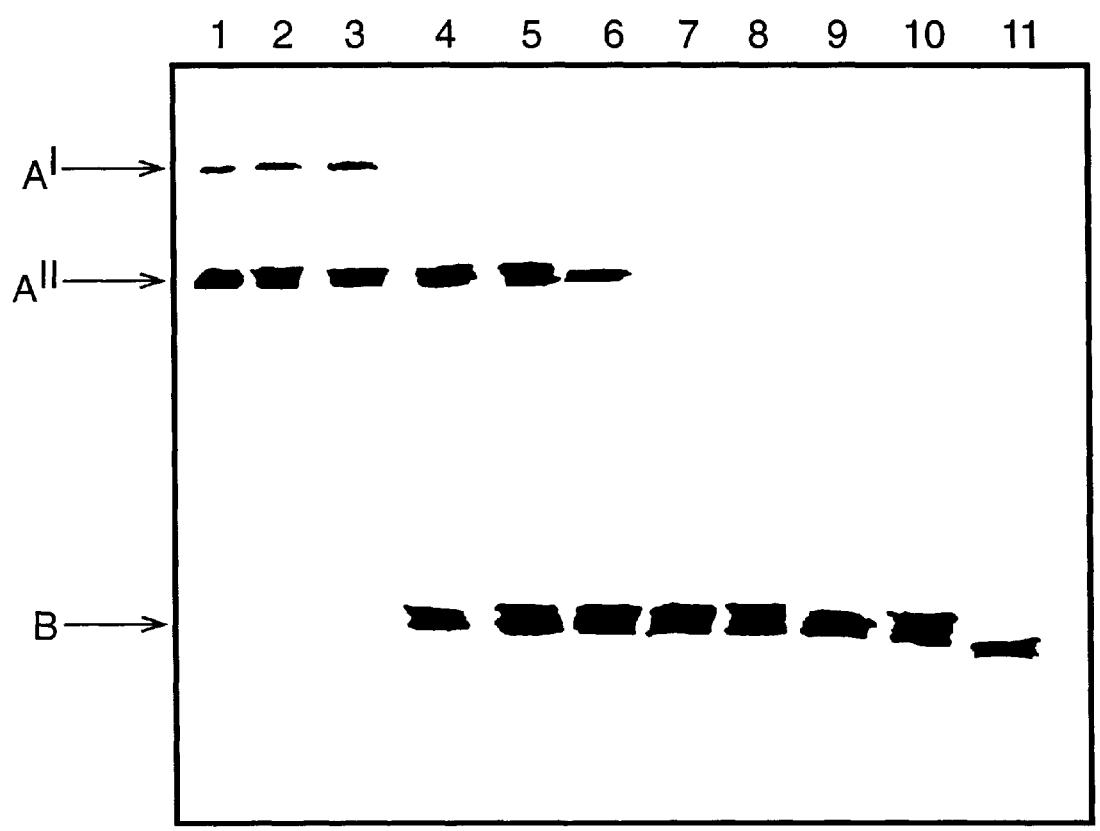
FIG. 1 is a schematic illustration of a DNA gel in which nondenatured or denatured plasmid DNA is detected.

The invention is based on the discovery of a scalable method for producing a high yield of pharmaceutical grade plasmid DNA. The method includes growing plasmid-containing cells to a high biomass while the cells are in exponential growth, and lysing the cells in the presence of detergent by raising the pH to a carefully controlled pH value in which maximal irreversible chromosomal DNA denaturation occurs but plasmid DNA is reversibly renatured at high yield. Generally, it has been found that the efficiency of recovery of plasmid DNA using prior art cell lysis methods decreases as plasmid size increases. In addition, plasmid DNA recovery is generally poorer according to prior art for plasmid DNA isolation methods at high culture biomass. The invention overcomes those drawbacks to the use of this process strategy for commercial manufacture of DNA. Pharmaceutical grade DNA produced according to the invention is useful in in vivo and ex vivo human gene therapy.

Cell Growth in Culture According to the Invention

A key feature of methods of the invention is providing a high biomass of cells which are in exponential growth, and performing the cell lysis step after the cell culture has been grown to high biomass. This is one way in which the inventive methods result in production of a large quantity of plasmid DNA.

The fermentation process described herein allows the volumetric yield of plasmid to be maximized. Two distinct methods are employed to achieve a high biomass culture which is in exponential growth, batch and fed-batch fermentation.

Batch fermentation allows the growth rate to be controlled through manipulation of the growth temperature and the carbon source used. As used herein, the term "batch fermentation" is a cell culture process by which all the nutrients required for cell growth and for production of plasmid contained in the cultured cells are in the vessel in great excess (for example, 10-fold excess over prior art concentrations of nutrients) at the time of inoculation, thereby obviating the need to make additions to the sterile vessel after the post-sterilization additions, and the need for complex feeding models and strategies.

Another type of fermentation useful according to the invention is fed-batch fermentation, in which the cell growth rate is controlled by the addition of nutrients to the culture during cell growth. As used herein, "fed-batch fermentation" refers to a cell culture process in which the growth rate is controlled by carefully monitored additions of metabolites to the culture during fermentation. Fed-batch fermentation according to the invention permits the cell culture to reach a higher biomass than batch fermentation.

An exemplary fermentation process and exemplary rates of feed addition are described below for a 50 L preparation. However, other volumes, for example 10 L, 50 L, or greater than 500 L, also may be processed using the exemplary feed rates described below, depending on the scale of the equipment used.

i) Inoculation

Cells are recovered from cryopreserved stocks (mid exponential or stationary phase cells snap frozen in LB medium supplemented with 20% sterile glycerol as a cryoprotectant) and streaked onto LBtet plates containing LB medium, 12 g /ml tetracycline and 1.2% agar. Single colonies from the plate are inoculated into 5–20 ml of LB medium supplemented with 12 g/ml tetracycline in sterile universal bottles or Erlenmeyer flasks and grown for 8–12 hours at 37° C. and 200 rpm in a shaking incubator. These cultures are then used to inoculate LBtet flasks (200–400 mL in 2 L Erlenmeyer flasks) at an inoculum concentration of 1%–5%. Sufficient flasks are inoculated to provide a 4% inoculum for the fermenter. These are grown at 37° C. and 200 rpm in a shaking incubator and used as an inoculum when in mid-exponential phase, typically after 5 hours at an OD600 nm of 1.5 units.

ii) Fermentation

The fermenter vessel used is a 50 L working volume Life Sciences Laboratories Ltd. 50/75 L P stirred tank bioreactor. Highly enriched batch medium and fed-batch medium fermentations are appropriate for the production of high cell density culture to maximize specific plasmid yield and allow harvest at high biomass while still in exponential growth.

Batch Fermentation According to the Invention

One example of a batch fermentation medium useful according to the invention is as follows.

The contents of a batch fermentation medium containing glycerol as a carbon source are as follows:

a) batch medium (in 46 L) sterilized in vessel

| component | g/L | |
|---|---|---|
| KH2PO4 | 3 | |
| Na2HPO4 | 6 | |
| Peptone(Gibco Select) | 10 | |
| NaCl | 0.5 | |
| (NH4)2SO4 | 5 | |
| Yeast Extract | 20 | |
| Trace elements solution | 0.5 mL | (the formulation of which is described below under Fed-Batch Fermentation according to the invention) | b) sterilized separately by autoclaving for post sterilization addition (psa) to the vessel

| MgSO4.72H2O | 0.7 g/L and |
|---|---|
| glycerol | 50 g/L | c) 0.2 μm filter sterilized for psa to the fermenter

| | | |
|---|---|---|
| Vitamins Solution | 0.5 mL | (the formulation of which is described below under Fed-Batch Fermentation according to the invention) |
| and | | |
| Tetracycline hydrochloride | 12 mg/L | |

Batch fermentation was carried out at 30° C. and pH 6.8. The pH was controlled by the automatic addition of 4M NaOH and 2.5M H2SO4. The dissolved oxygen (DO) setpoint was 20% of saturation and was controlled by the automatic adjustment of the fermenter agitation speed. Throughout the fermentation, samples were taken for measurement of optical density (OD600 nm) and glycerol concentration. Cell pellets from each sample were collected by centrifugation and stored at −20° C. for subsequent analysis of plasmid yield.

For batch fermentation, the inventive methods are advantageously used with glycerol as the carbon source. This reduces acetate formation and allows the culture to grow at its maximum specific growth rate, $\mu$max for the duration of the fermentation. The growth on glycerol at 30° C. typically gives a $\mu$max of below 0.3 which is sufficient to stop significant acetate accumulation and prevents plasmid instability associated with high growth rates.

In addition, for batch fermentation, the inventive methods are more advantageously used to achieve higher cell densities with glycerol as a carbon source, rather than the conventional carbon source of glucose. That is, the culture may be grown at a higher concentration of glycerol than glucose due to the comparative inhibitory effects of glucose and glucose metabolites on cell growth. Cell growth is inhibited where glucose is the carbon source at much lower concentrations of glucose than glycerol. Glucose is also less soluble in the culture medium than glycerol (which is a liquid at room temperature) limiting the amount of glucose which can be added to the batch fermentation medium. Thus, higher cell densities are achieved where glycerol is the carbon source in comparative cultures using identical concentrations of glucose and glycerol.

Using batch fermentation in glycerol-based culture, the biomass levels achievable generally do not exceed 30 g cells/L dry weight. It is for this reason that fed-batch culture fermentation is preferred, i.e., fed-batch fermentation allows the culture to attain a higher cell biomass prior to lysis. Fed-batch fermentation according to the invention permits the exponential growth phase of the culture to be extended, and thus an increase in the biomass level during exponential growth.

Fed-Batch Fermentation According to the Invention

In one example of a fed-batch fermentation according to the invention, glucose or glycerol may be used as a carbon source. A fed-batch fermentation medium in which glucose is the carbon source is described below. Added to the fermenter vessel in 46 L of deionized water are the following reagents:

| component | g/L |
|---|---|
| KH2PO4 | 5 |
| (NH4) 2HPO4 | 3 |
| Peptone (Gibco Select) | 5 |
| Yeast Extract (Gibco Select) | 5 |

-continued

| component | g/L |
|---|---|
| NaCl | 0.5 |
| Trace elements solution | 2 ml/1 |

Added aseptically post sterilization:

| | |
|---|---|
| D-glucose (sterilized by autoclaving) | 0.7 g/l |
| Thiamine hydrochloride (filter sterilized) | 6 mg/1 |

The trace elements solution comprises:

| Component | g/L |
|---|---|
| ZnCl2.4H2O | 2 |
| CoCl2.6H2O | 2 |
| Na2MoO4.2H2O | 2 |
| CuCl2.2H2O | 1.9 |
| H3PO3 | 1.6 |
| MnSO4.H2O | 1.6 |
| Citric acid | 60 |
| FeSO4 | |
| CaCl2.2H2O | 1 |
| AlCl3.6H2O | 0.4 |

The vitamin solution comprises:

| Component | g/L |
|---|---|
| L-biotin | 0.06 |
| Folic acid | 0.04 |
| Pyridoxine.HCl | 1.4 |
| L-riboflavin | 0.42 |
| L-niacin | 6.1 |
| L-pantothenic acid | 5.4 |

Feed medium (each component autoclaved separately and aseptically mixed prior to use).

| Component | g/L |
|---|---|
| D-glucose | 500 |
| MgSO4.7H2O | 6.1 |
| (NH4)2SO4 | 17.9 |

All media components are sterilized at 121.3° C. and 1 bar over atmospheric pressure for 30 minutes. Fermentations (i.e., cell growth) may be carried out at 37° C. and at pH 6.8. The pH is controlled by the automatic addition of 4M NaOH and 2.5M H2SO4. The dissolved oxygen (DO) setpoint is 50% of saturation and is controlled by the automatic adjustment of the fermenter agitation speed. Throughout the fermentation, samples are taken for measurement of optical density (OD600 nm) and glucose concentration. Cell pellets from each sample are collected by centrifugation and stored at −20° C. for subsequent analysis of plasmid yield.

The fermentation is run in batch mode until the initial carbon substrate (glucose) is exhausted. This point is noted by a sudden rise in DO and confirmed by glucose analysis of a sample taken immediately after this event. The previously primed feed medium pump is then started. The pump rate is determined by a model derived from Curless et al. (Bioeng. 38:1082–1090, 1991), the whole of which is incorporated by reference herein. The model is designed to facilitate control of the feed phase of a fed-batch process. In the initial batch process, a non-inhibitory concentration of substrate is consumed by cells growing at their maximum specific growth rate, max, giving a rapid rise in the biomass levels after inoculation. The culture cannot grow at this rate indefinitely due to the accumulation of toxic metabolites (Fieschio et al., "Fermentation Technology Using Recombinant Microorganisms." In *Biotechnology*, eds. H. J. Rhem and G. Reed. Weinheim: VCH Verlagsgesellschaft mbH 7b: 117–140, 1989). To allow continued logarithmic growth, the model calculates the time-based feed rate of the growth-limiting carbon substrate, without the need for feedback control, to give a fed-batch phase of growth at a set by the operator. This is chosen at a level which does not cause the build up of inhibitory catabolites and is sufficient to give high biomass. In this fermentation, a of <0.2 is appropriate for cultures using glucose as the substrate.

The feed rate calculated to extend the growth phase is derived using the equation:

$$F_o = \mu V_b X_b / S_{fo} Y_{SX}$$

where:

$F_o$ is the feed rate at time zero in L/h (initial feed rate);
$\mu$ is the specific growth rate;
$V_b$ is the batch volume in the vessel in L;
$X_b$ is the amount of biomass produced after the initial batched amount of substrate is exhausted, in g/L;
$S_{fo}$ is the amount of substrate in the initial batch volume in g/L; and
$Y_{SX}$ is the yield coefficient of the organism grown on the substrate, i.e. $Y_{SX} = r_X / r_s$ where $_x r$ is the volumetric rate of biomass production and $r_s$ is the volumetric rate of substrate consumption, thus giving $Y_{SX}$ units of g/g/h.

After two hours of feeding, due to the increasing cell concentration in the vessel, it is necessary to adjust the initial feed rate to compensate for the exponentially increasing biomass level in the vessel, which results in an exponentially increasing demand for substrate.

The equation used to adjust the feed rate after two hours is $$F = F_o e^{\mu t}$$

where:
F is the feed rate in L/h;
$F_o$ is the initial feed rate;
$\mu$ is the required specific growth rate; and
t is the time after the start of feeding at $F_o$.

The feed rate is adjusted every hour using the above equation until the desired harvest $OD_{600nm}$ is reached.

Where methods of the invention utilize a fed-batch process that controls $\mu$, either directly by controlling the rate of addition of a growth limiting substrate, or indirectly by lowering the growth temperature and manipulating the carbon source, the plasmid yield (plasmid copies/cell or mg plasmid DNA/g bacteria) may be optimized by optimizing the growth of the cells. By controlling and harvesting during the controlled and extended exponential growth phase or linear phase, plasmid quality is controlled and plasmid instability is reduced.

Cell growth also may be carefully controlled according to the invention by ensuring that cellular precursors do not become limiting in the culture medium. For example, in a starved *E. coli* culture, protein synthesis can be shut down (the stringent response), but plasmid DNA replication may continue. It has been shown by Blair et al. (Proc. Nat. Acad. Sci., U.S.A. 69:2518–2522, 1972) that when protein synthesis is inhibited (by the addition of chloramphenicol), plasmid synthesis is maintained for up to 20 hours (Clewell et al., Bacteriol. 110: 1135–1146, 1972). However, the isolated plasmids from this preparative procedure are sensitive to high pH and to certain ribonucleases, indicating that they contain one or more ribonucleotides as part of their covalently-closed double stranded structure. Such ribonucleotide incorporation into plasmid DNA causes denaturation during the alkaline lysis and RNAase treatment steps of plasmid DNA purification protocols (e.g., Birnboim et al., Nucl. Acids Res. 7:1513–1523, 1979; Birnboim, Methods Enzymol. 100:243–255, 1983). Therefore, it is advantageous according to the inventive methods for nucleic acid and protein synthesis precursors to be maintained at non-limiting levels in the feed medium to maintain plasmid yield and quality at increasingly high cell density.

Therefore, in a batch fermentation according to the invention, high levels (e.g., 4-fold higher than prior art concentrations) of precursors are present in the enriched batch medium. In particular the quantities of yeast extract in the batch medium enriched form 5 g/l (as in LB medium) to 20 g/liter thus providing huge quantities of growth factors and nucleic acid precursors. The medium is also supplemented with ammonium sulfate (5 g/l) which acts as a source of organic nitrogen.

The additions of precursors (organic nitrogen in the form of ammonium sulfate) during the feeding process in fed-batch fermentation are designed to prevent deleterious effects on plasmid quality.

Table 1 presents data in which different transformed host strains are grown in 50 L glucose fed-batch fermentations (as described below). *E. coli* host strains HB101, DH1 and DH5 F transformed with model plasmid backbone pUC18Tet (FIG. 2) are compared in Table 1 with respect biomass yield, plasmid yield and growth characteristics.

TABLE 1

| Host Strain | Maximum OD600 nm Fed batch | Plasmid Yield (mg/l) | Comments | Source |
|---|---|---|---|---|
| HB101 | 20–25 | 0.51 mg/l (Or 0.2 mg/OD/l) | No lag | ATCC 33694 |
| DH1 | 20 | 0.47 mg/l (Or 0.23 mg/OD/l) | 7 hr lag phase | ATCC 33849 |
| DH5α | 32 | 0.16 mg/l (Or 0.07 mg/OD/l) | 5 hr lag phase | Life Technologies Cat. No. 18265-017, part no. 98258 |

Table 1 shows that host strain DH5 grows to the highest biomass, but gives the lowest specific plasmid yield. DH1 and B101 give similar plasmid yields, but the biomass reached by DH1 is lower.

Monitoring of Plasmid Yield, Plasmid Stability and Plasmid Loss According to the Invention In order to determine whether the fermentation process used in the invention is permitting production of plasmid in the cultured host cell, plasmid yield, stability and loss may be monitored during cell growth or after cell lysis. Evidence of plasmid loss (segregational instability) during fermentation is monitored by the following methods:

i) Duplicate plating of a freshly diluted fermented sample on LB agar plates and LBtet agar plates in triplicate. *E. coli* clones which have lost all copies of the tetracycline resistance-carrying plasmid will not grow on LBtet media and counts are compared to estimate the percentage stability at each time point.

ii) Alkaline lysis minipreps (Birnboim et al., Nucl. Acids Res. 7:1513–1523, 1979; Birnboim, Methods Enzymol. 100:243–255, 1983) and agarose gel electrophoresis of fermentation samples normalized to 1 OD600 unit. Relative intensity of the plasmid bands throughout the culture can be visualized and compared on the gel. Relative amounts of supercoiled, open circle, multimers and denatured plasmid can also be visualized. Agarose gels also give data on a second type of plasmid instability, structural instability due to deletion, insertion or rearrangement. If structural instability is suspected, a diagnostic restriction endonuclease map may be used to confirm where structural integrity has been altered or lost. No plasmid instability was detected with the strains and plasmids evaluated, but the relative proportions of the different plasmid forms (supercoiled, open circle and multimers) varied with strain and plasmid type. Plasmid multimers are most common in DNA purified from DH5.

The relative plasmid yield and copy number for each host strain may be compared by a qualitative slot blot hybridization assay. A total DNA extraction may be performed on each normalized sample. DNA is bound to a nylon filter using a slot blot apparatus as described in Current Protocols in Molecular Biology, eds., Ausubel et al., John Wiley and Sons, Inc. U.S.A., 1995. The slot blot is hybridized with 32p labeled plasmid and single copy chromosomal gene DNA probes. Relative plasmid yield and copy number can therefore be estimated by scintillation counting of the filter slots. Plasmids yields from DH1 and HB101 are consistently higher than from DH5.

Host Cell Lysis and Plasmid Purification According to the Invention

A key aspect of methods of the invention is cell lysis. Methods of the invention include a cell lysis step in which host cells are lysed using a carefully controlled rise in pH to a value that is determined based on the denaturation characteristics of the plasmid DNA. Prior to the cell lysis step, the fermentation culture may be prepared for lysis as follows.

When the desired OD600 nm of the culture is reached, (as measured off-line in a spectrophotometer), for example, this OD may be of the order of 30–60, the culture is ready for harvest (OD600>60), the fermentation broth is chilled to <10° C. and concentrated to 10 L by standard cross-flow filtration using, for example, a Filtron Centrisette equipped with 100,000 molecular weight cut off or 0.2 polysulphone membranes. The concentrate is then diafiltered against 50 L of a buffer (cell resuspension buffer) such as 50 mM Tris-HCl, 10 mM EDTA, pH 8.0. At this stage the process stream has an equivalent to 3.5–5.5 kg of biomass (wet weight) containing 1–5 g of plasmid DNA depending on the vector used. The cell slurry obtained at harvest may be stored frozen (<−20° C.) or the cells lysed immediately.

Alternatively, the contents of the fermenter may be aseptically decanted into 1000 ml centrifuge bottles and the cells separated by centrifugation and collected as cell pellets. The supernatant is discarded and the pellets frozen (<−20° C.) or the cells lysed immediately.

Alternatively, the contents of the fermenter may be collected as a slurry by continuous centrifugation. The supernatant is discarded and the slurry frozen (<−20° C.) or the cells lysed immediately.

Cell lysis is performed at a pH value which is close to but does not reach the irreversible alkaline denaturation pH value of the plasmid DNA. Cell lysis and plasmid DNA purification may be performed as follows.

1. Cell Lysis and Primary Recovery of Plasmid DNA

Lysis of host cells is performed once cells are resuspended at an OD600 equivalents of between 20 and 100, but ideally 30–40 in a buffer containing bovine RNase (100 mg/l), alkali, and sodium dodecyl sulfate. A key feature of methods of the invention is that the lysis step is performed under carefully controlled pH conditions.

According to the invention, any alkaline base that is capable of denaturing chromosomal DNA may be used; for example hydroxide salts, such as potassium hydroxide (KOH), lithium hydroxide (LiOH), or sodium hydroxide (NaOH).

The lysis step involves (i) slow addition of alkali to the cultured cells, and (ii) careful monitoring of rising pH value of the lysate using a pH meter. Proper performance of these steps according to the invention involves, in most cases, determination of that pH value during lysis of a suspension of host cells containing the plasmid at which no more than approximately 50% of the plasmid DNA is irreversibly denatured as visualized by agarose gel electrophoresis, and by carefully controlling the rise in pH during lysis in the culture such that the pH does not rise above that level, and preferably does not exceed 0.1 pH units below that value. These steps minimize the formation of irreversibly denatured plasmid species, which rapidly occurs at high pH values.

Where the rise in pH during lysis causes a sharp transition from reversibly to irreversibly denatured plasmid, and it is difficult to determine the pH value during lysis at which no more than about 50% of plasmid DNA is irreversibly denatured, but it is possible to determine the pH value during lysis at which no more than about 90–95% of the plasmid DNA is irreversibly denatured, one can select a pH value to produce a relatively high yield of plasmid DNA which is about 0.17–2.0 pH units below the pH at which no more than about 90–95% of plasmid DNA is irreversibly denatured.

The irreversible denaturation value of a plasmid is determined as follows.

The pH value at which irreversible denaturation rapidly occurs is a property of the denaturation characteristics and size of the plasmid. The inventive methods are critically dependent on and sensitive to, i.e., to ±0.05 pH unit, the pH value at which the cells are lysed. This final pH value can be determined from denaturation studies on the purified plasmid. If the pH is too high, the plasmid is irreversibly denatured to a form with high mobility on gel electrophoresis, is biologically inactive and displays resistance to degradation by restriction endonucleases. This irreversibly denatured plasmid is generally recovered with low yield during the subsequent purification stages and in some cases may be irretrievable leading to very low plasmid DNA yields from cells lysed at a pH which is too high. Therefore, in determining the amount of irreversibly denatured plasmid DNA present an estimate of the amount of irreversibly denatured plasmid DNA which was irretrievable is also made. The total irreversibly denatured plasmid DNA is thus the sum of denatured plasmid DNA recovered plus the denatured DNA which was irretrievable. In practice a measure of irretrievable plasmid DNA can be made by estimating the difference between plasmid DNA yield after lysis of cells containing plasmid DNA at the optimum pH, where DNA yield is maximum and there is little or no denatured plasmid DNA (as visualized by agarose gel electrophoresis after DNA purification) and the DNA yield under the test conditions where pH at lysis is sub-optimal. DNA yields can be calculated by, for example, measuring the optical density at 260 nm of a measured sample volume from all the plasmid DNA purified in an experiment, and calculating the plasmid DNA concentration using the extinction co-efficient for plasmid DNA as is well known to one skilled in the art. The total yield is the product of the concentration and the total volume.

If the pH is too low, the chromosomal DNA will not be fully denatured and levels of contaminating chromosomal DNA will be unacceptably high in the final purified plasmid DNA product. Therefore, the critical pH value for a given plasmid is determined in a testing sample of the culture by varying the pH at which cell lysis is performed, and determining that pH value which gives about (i.e., about equal to but no more than) 50% denaturation of the plasmid DNA. For example, one relatively easy method of determining the pH value at which 50% of the plasmid DNA is irreversibly denatured is to take samples of cell culture during lysis as the pH is undergoing a carefully controlled rise of 0.1 pH units per step, neutralizing each sample, and running the sample on a standard agarose gel. Therefor, where the pH rises in 0.1 unit intervals between, for example, 12.0 and 12.9, a gel is generated in which the lanes correspond to each sample taken at a given pH value during cell lysis. Control lanes may include a low pH value, e.g., pH 11, at which all plasmid DNA remains in a position indicating no plasmid denaturation, and a high pH value, for example 14.0, at which all plasmid DNA has migrated low in the gel to a position indicating substantially all plasmid DNA has irreversibly denatured. The remaining lanes, corresponding to successive rises in pH during lysis, will indicate no plasmid denaturation (e.g., supercoiled (closed circular) plasmid DNA) at pH values below the irreversible alkaline denaturation value, or increasing amounts of irreversibly denatured plasmid DNA at pH values above the irreversible denaturation value. For each plasmid DNA, 50% of plasmid denaturation will occur within a change in pH of 0.1–0.3 units. For most plasmids, this pH change at which 50% of plasmid DNA is denatured will span only 0.1–0.2 pH unit difference, and may span only 0.1 pH unit difference.

As used herein, the pH value at which about 50% of plasmid DNA is irreversibly denatured is the "irreversible denaturation value" of the plasmid. The optimal pH for host cell lysis according to the invention is that pH which is 0.1 and preferably 0.2 pH units below that pH at which 50% of the plasmid DNA is irreversibly denatured, or 0.17–0.20 pH units below the pH at which 90–95% of the plasmid DNA is denatured.

FIG. 1 is a schematic illustration of a DNA gel in which plasmid DNA from a sample aliquot of a representative cell culture is loaded into each lane of the gel. Lane 1 represents lysis of host cells at pH 11, a pH at which all plasmid DNA is expected to remain undenatured; lanes 2–10 represent sample lysis at pH 12.0, 12.2, 12.3, 12.4, 12.5, 12.6, 12.7, 12.8, and 12.9, respectively; and lane 11 represents lysis of host cells at pH 14.0, a pH at which substantially all plasmid DNA is expected to be denatured. In lane 1, undenatured plasmid DNA is represented by a single band (A") or a double banding pattern (A' and A") near the top of the gel. A" indicates the position to which supercoiled plasmid (closed circular DNA) migrates. A' indicates the position to which open circular (nicked) DNA migrates. A' and A" together are undenatured plasmid DNA. In lane 11, fully denatured plasmid DNA is represented by a single band (B) near the bottom of the gel. Therefor, B represents the position to which irreversibly denatured plasmid DNA migrates. In test sample lanes 2–10, plasmid DNA migrates as one or more bands, corresponding to undenatured DNA or irreversibly denatured DNA. In FIG. 1, the pH value at which approximately 50% of plasmid DNA is undenatured (A' and A") and 50% is irreversibly denatured (B) is indicated by the change in migration of this representative plasmid DNA between pH 12.3 and 12.4. Therefor, pH 12.4 is considered the irreversible alkaline denaturation value for the representative plasmid. The pH of the lysis step for the corresponding cell culture is then 0.1 pH units below pH 12.4, i.e., at pH 12.3, or more preferably, it is 0.2 pH units below pH 12.4, i.e., at pH 12.2.

It is expected that most plasmids useful according to the invention will be characterized in that their irreversible alkali denaturation pH will be between 12.1 and 12.9. Therefor, the actual pH value chosen for cell lysis will be 0.1 and preferably 0.2 pH units below the point at which irreversible denaturation of the plasmid DNA occurs. The pH value between 12.1 and 12.9, at which much of the plasmid DNA is reversibly renatured, and chromosomal DNA is denatured, is the critical pH value for cell lysis of cells containing that plasmid.

In one embodiment of the methods of the invention, the pH needed to bring about cell lysis is rapidly brought to approximately just below pH 12.0 and then the pH is adjusted slowly by dropwise addition until it is at a pH value between 12.1 and 12.9 which is just below the irreversible alkaline denaturation value of the plasmid.

In another embodiment, the concentration of the sodium hydroxide solution needed to bring about adjustment of the lysate to the optimal pH is calculated from small scale experimentation and the requisite amount of alkali added to the cells without further pH adjustment, for example, adding an amount of sodium hydroxide to the cell culture that is in the range of 0.1 to 0.2 M. It can be relatively difficult to measure pH accurately and precisely in viscous, and often heterogeneous cell lysates without removing a sample and mixing it well by, for example, homogenization before a pH measurement is recorded. Such mixing shears plasmid DNA and thus destroys the sample. This measurement cannot therefore be made directly and on-line' during a manufacturing process but must be made off-line' and the sample subsequently discarded. Therefore, a preferred embodiment of the invention is to perform a series of small lysis experiments where cells are treated with lysis buffer containing 0.14M NaOH or more in 0.05M or 0.1M steps. After purification of the plasmid, agarose gel electrophoresis is performed as above, as visualized by Ethidium Bromide-staining and UV-fluorescence, and the conditions where about 5% or more irreversibly denatured plasmid are identifiable. The optimum NaOH concentration is generally 0.015M to 0.03M lower than this test condition. In this way it is possible to titrate the NaOH concentration (and thus pH) in the lysis solution to identify the optimum pH value for that plasmid (and host vector combination).

In another preferred embodiment, lysis is achieved by treating the cells with 0.075M NaOH and 1% SDS to raise the pH to approximately 11.9. This is followed by adjusting the pH slowly with dropwise addition of 5M NaOH to a predetermined pH value of between pH 12.1 and 12.9 depending upon the irreversible denaturation characteristics of the plasmid being isolated.

Primary recovery of plasmid DNA is facilitated using modification of the methods of Birnboim et al. (Nucl. Acids Res. 7:1513–1523, 1979) and Birnboim (Methods Enzymol. 100:243–255, 1983), the contents of which are incorporated by reference herein.

After up to 30 minutes of alkali extraction, 3M potassium acetate, pH 5.5, is slowly added to the denatured extract, and the solution forms a heavy precipitate. In order to minimize plasmid DNA degradation, it is important that this precipitate, which contains irreversibly denatured chromosomal DNA, RNA, and protein, be removed using a method that minimizes shear forces, for example, a commercial bag filter, such as a 15–900 woven mesh of polypropylene, nylon or the equivalent, as described below.

Optionally, the filtrate may be further clarified by depth filtration using a commercially available system such as Pall 10 uncharged polypropylene Profile depth filters or the equivalent.

RNA may be reduced by further ribonuclease treatment by the addition of sufficient ribonuclease to attain a concentration of up to 100 mg/l.

In another embodiment of the invention, 1 volume of the cell suspension at optical density at 600 nm of 20–100 is treated with 2 volumes of the lysis buffer containing the optimum sodium hydroxide concentration determined in small scale experiments. This allows more efficient lysis at high cell concentrations and also results in a more consistent and uniform precipitate when treated with one volume of 3M potassium acetate (KAc) at pH 5.5. This precipitate contains irreversibly denatured chromosomal DNA, RNA, protein and other contaminants entrapped in the body of the precipitate. By use of the optimum sodium hydroxide concentration in the lysis buffer, the lysis time may be continued for up to 30 minutes without detriment to plasmid quality as determined for each plasmid in small scale experiments. In this embodiment, the addition containing the optimum sodium hydroxide concentration of two volumes of the lysis buffer added to 1 volume of cell suspension may allow better clearance of some of the contaminants due to increased contact with a higher overall concentration of sodium hydroxide.

2. Anion Exchange Chromatography

Cellular debris and soluble contaminants and residual RNA are removed using an anion exchange chromatography step. The coarse filtered extract (60 L) can be mixed with 15 L of a low ionic strength, non-phosphate buffer such as 25 mM potassium acetate, pH 5.5, or 25 mM Tris-HCl, pH 8.0, such that the conductivity of the process fluid is between 40 and 100 mS, preferably between 55 and 65 mS.

The fluid is then applied to a vessel containing an appropriate anion exchange matrix. A preferred matrix is Pharmacia Streamline DEAE used in an expanded or fluidized bed modality.

In both the expanded and fluidized bed modalities, the loading concentration should be about 50 g to about 100 g plasmid DNA/ml of gel. Any gel may be used that is macroporous enough to permit unhindered diffusion through the gel and hydrophilic enough such that it has a low affinity for DNA and thus has low non-specific binding for DNA. The Pharmacia Streamline Gel is a macroporous agarose based anion exchange matrix which is ideally suited to DNA purification. This type of matrix permits high recoveries and little non-specific adsorption of plasmid DNA on the matrix. Many other commercially available anion exchange matrices such as Hyper D (BioSepra) and Source 30 (Pharmacia) are poorly suitable for preparative plasmid DNA chromatography as they do not possess these attributes. In these cases a significant proportion of the plasmid DNA is non-specifically bound to the matrix and smears across the majority of the eluted column fractions.

In addition, the Streamline matrix is designed for use in the expanded bed modality. This configuration is particularly advantageous for DNA separations in that expanded bed chromatography allows the loading solution to contain solid particles of <60 m in size. Plasmid DNA separations which rely on an expanded bed are able to operate efficiently in the presence of colloidal precipitates which are difficult to completely remove by membrane filtration, and thus expanded bed chromatography provides a useful unit operation which leads to a simpler process and therefore increased yield because loss in yield may occur if additional filtration is required. Indeed plasmid DNA is a large molecule, and fine filtration, for example 0.2 m filtration, of such large species is not achievable without significant loss due to, for example, binding of DNA to the filter matrix, or clogging of the filter matrix.

Another advantage of a fluidized bed is the relatively high flow rates used during the chromatographic process. Such rates are not always achievable with conventional column chromatography. This again leads to a quicker process which is easier to operate. In this configuration the amount of gel required is within the range of 10 g to 1 mg plasmid DNA per ml gel. A column with an aspect ratio of 5:1 (length:diameter) is fitted with 60 m sinters at the top and bottom of the column. The column is equilibrated by directing the flow upward at a linear flow rate of 100–160 ml/h. After equilibration the process stream is applied to the matrix in the same flow orientation at the same flow rate. In some cases it may be necessary to recycle the process solution around the column until all the plasmid DNA has been adsorbed. The bed is then washed with buffer in the same way until any particulate material has been removed and the eluate is clear. A low ionic strength buffer, such as the 25 mM potassium acetate pH 5.5 or 25 mM Tris-HCl pH 8.0 buffer employed above, may be used to wash the matrix bed until the solids contamination has reached a minimum. The flow is then reversed i.e. in a downward direction at the same flow rate.

The upper head of the column is then moved to just above the top of the packed bed and the now conventionally packed column eluted with the elution buffer. The column may be eluted successively with buffers of increasing ionic strength, or in a single elution step. The buffers are preferably made by adjusting an appropriate low ionic strength buffer of pH values between 5.0 and 8.0 to approximately 0.1M, 0.3M, 0.5M, 0.075M, 1M and 1.5M with respect to sodium chloride. Contaminating RNA can optimally be removed in the 0.5M buffer wash. Plasmid DNA is eluted in the 0.75M to 1.0M wash. The plasmid DNA fractions, now substantially depleted with respect to their RNA content, are collected.

3. High Resolution Anion Exchange Chromatography

The use of high resolution anion exchange chromatography as a step in plasmid DNA purification is optional in the invention, as it is not required to achieve pharmaceutical grade DNA as described according to the invention. However, if desired, this step may be added to the purification process as follows.

Residual RNA, chromosomal DNA and protein, and endotoxins, can be further reduced and the plasmid DNA concentrated by high resolution ion-exchange chromatography. The 7–14 liters of eluate from the previous step are diluted 13-fold with deionized water or low ionic strength buffer and applied to 2–10 L column of an appropriate anion exchange matrix, such as Pharmacia Source 30Q or Bio-Sepra HyperD Q. Optionally, a detergent, such as Triton X-100 or Tween 20(0.1–1% v/v), may be added to the buffers to aid in the removal of endotoxin proteins. The column is eluted with appropriate buffers such as 0–3M sodium chloride gradient in 10 mM Tris-HCl, 1 mM EDTA buffer, pH 8.0. Residual RNA elutes first, followed by plasmid DNA eluting at an ionic strength of approximately 0.7–1.5M sodium chloride.

4. Gel Permeation Chromatography

Traces of RNA, protein and remaining endotoxin are removed by gel filtration. This step also serves to exchange the plasmid product into a pharmaceutically acceptable solution.

The eluate from the previous step is concentrated either by precipitation with polyethylene glycol or cross flow filtration to a volume of less than 1.0 L. The concentrate is then applied to a 7–8 L column of an appropriate gel filtration matrix, such as Pharmacia Sephacryl S-1000 or S500HR. The size of the capacity of the column is in the range of 1 g–50 g plasmid DNA/ml of gel. The first major peak to elute is the plasmid DNA product. The equilibration and elution buffer for this column can be any buffer suitable for the formulation of plasmid DNA, but preferably sodium bicarbonate (2 g/L, pH 7.5) containing sodium chloride (6 g/L).

The plasmid DNA solution is then preferably diluted to a concentration of 0.1 to 1.0 mg/ml with sterile buffer and filtered through a 0.22 or 0.45 membrane filter and stored at a temperature of 4° C. to −80° C.

The quality of the final plasmid isolation may be tested using the following criteria:

| | |
|---|---|
| Appearance: | Clear, colorless solution |
| Form: | Percentage closed circular, open circular, multimer and linear forms as determined by gel electrophoresis. |
| Stability: | Size and restriction pattern consistent with original construct. |
| E. coli DNA: chromosomal | Less than about 1–5% contaminating DNA as judged by PCR. |
| RNA: | Not detectable as determined by agarose gel electrophoresis. Quantified by HPLC as <0.2% w/w. |
| Endotoxin: | Levels below 100 EU/mg plasmid DNA. |
| Protein: | Not detectable when determined by silver stained sodium dodecyl sulfate polyacrylamide gel electrophoresis ( SDS PAGE). |

Vectors and Host Cells Useful According to the Invention

Vectors useful according to the invention include a vector that possesses the following characteristics:

i) High copy number bacterial origin of replication.

Vectors having relatively high copy number, i.e., in the range of 20–40 copies/cell up to 1000–2000 copies/cell, are especially useful according to the invention. For example, a vector that includes the pUC origin of replication is preferred according to the method of the invention. The pUC origin of replication permits more efficient replication of plasmid DNA and results in a tenfold increase in plasmid copy number/cell over, e.g., a pBR322 origin. The resulting high copy number greatly increases the ratio of plasmid DNA to chromosomal DNA, RNA, cellular proteins and co-factors, improves plasmid yield, and facilitates easier downstream purification.

ii) Small and stable vector backbone.

It is preferred according to the invention that the backbone of a vector used according to the methods described herein be small, i.e., less than 5 kb, and preferably 1–3 kb. The term "vector backbone" refers to the bacterial DNA necessary to maintain and propagate the vector in a bacterial host. Vectors of the invention which include both backbone and insert will be on the order of 15–50 kb in size, or even larger. Thus, a vector backbone useful in the invention will be capable of carrying inserts of approximately 10–50 kb or larger. The insert may include DNA from any organism, but will preferably be of mammalian origin, and may include, in addition to a gene encoding a therapeutic protein, regulatory sequences such as promoters, poly adenylation sequences, enhancers, locus control regions, etc. The gene encoding a therapeutic protein may be of genomic origin, and therefore contain exons and introns as reflected in its genomic organization, or it may be derived from complementary DNA.

The vector should also be stably inherited; that is, the vector backbone preferably contains no intrinsically unstable elements prone to rearrangement, deletion, etc, such as transposons, and is stably inherited in the presence of the selective agent.

Figure 2:
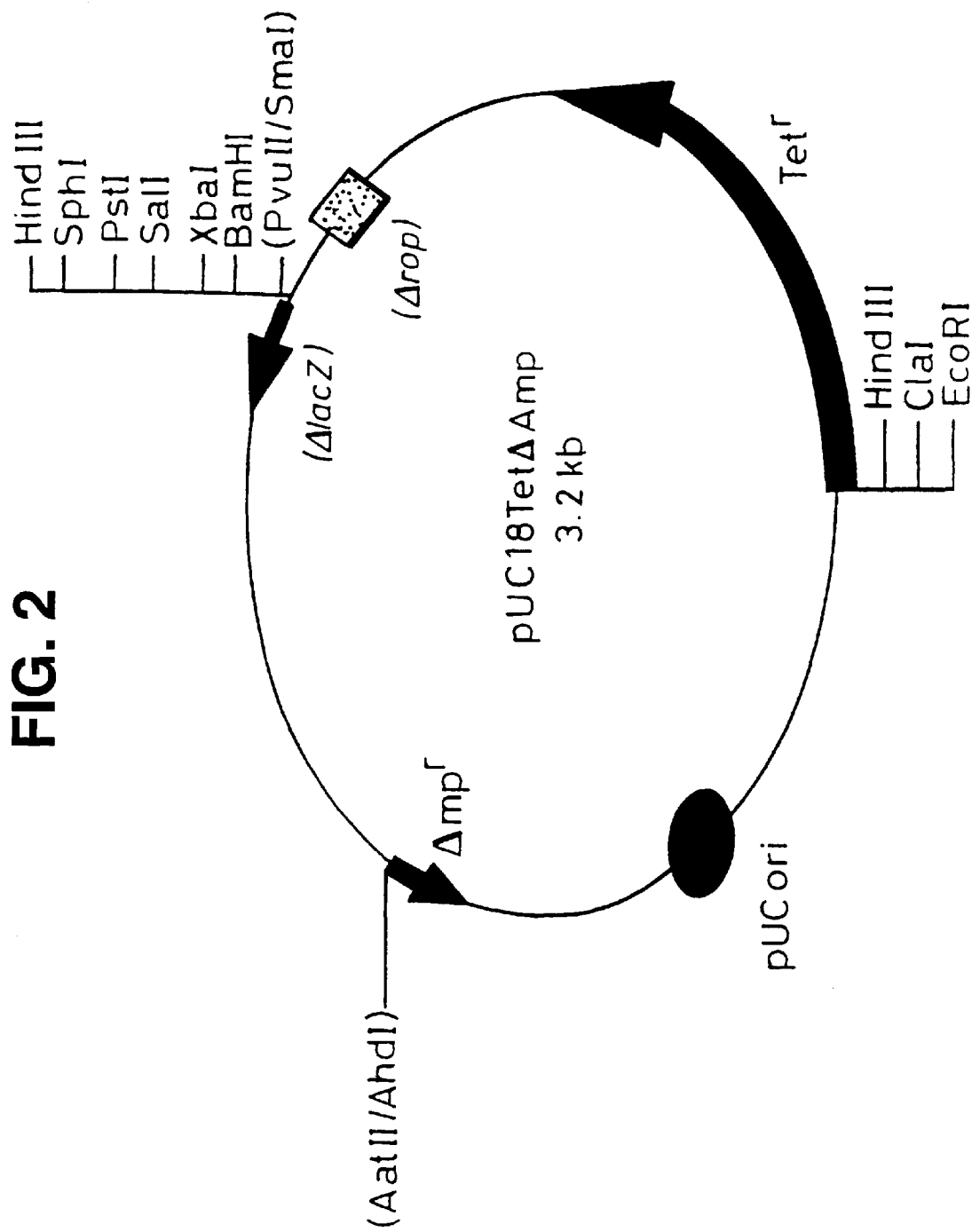
FIG. 2 is a plasmid map of plasmid pUC18tetΔAmp.
Figure 3:
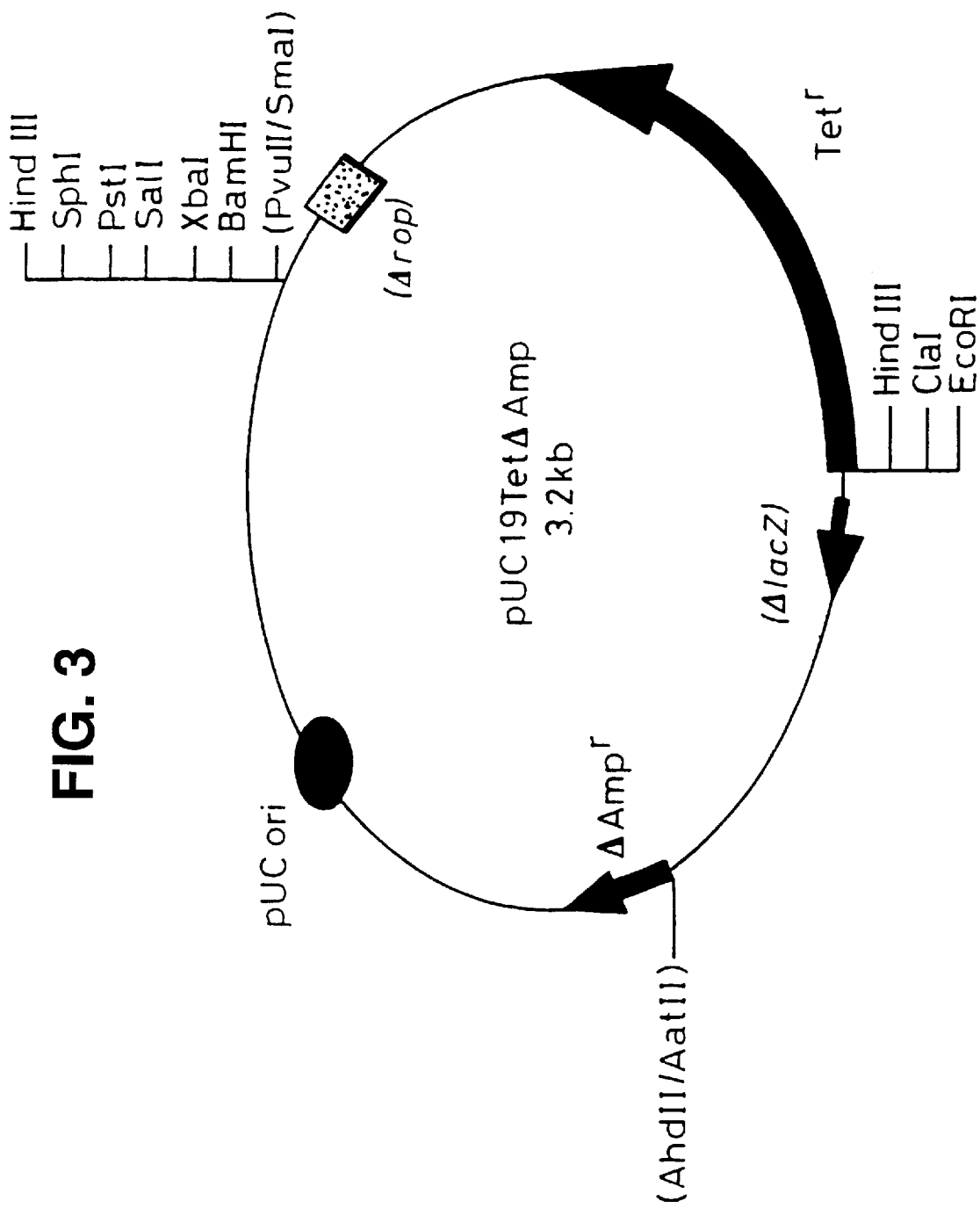
FIG. 3 is a plasmid map of plasmid pUC19tetΔAmp.

Any vector (plasmid DNA) may be used according to the invention. Representative vectors include but are not limited to pUC18/19tet Amp, pUC19tet, pTX0118, pTX0161, pTX0100 and pTX0201. An exemplary plasmid vector backbone suitable for carrying a mammalian therapeutic gene and regulatory sequences is shown in FIGS. 2 and 3. These vectors were designed and constructed for propagation in E. coli host strains.

Plasmid Vector Backbones pUC18Tet Amp and pUC19Tet Amp

1. Construction of pUC18Tet and pUC19Tet Vectors

These vectors were generated from insertion of the EcoRI-PvuII restriction endonuclease fragment of pBR322 (Bolivar, F. et al.(1977) Gene 2,95) containing the tetracycline resistance gene into EcoRI-SmaI cut pUC18 and pUC19 (Viera, J. and Messing, J., Gene 19, 259 (1982) and Yaniscch-Perron, C. Et al., Gene 33, 103 (1985) respectively.

2. Construction of pUC8Tet Amp and pUC19Tet Amp Vectors pUC18Tet Amp and pUC19Tet Amp were derived from pUC18Tet and pUC19Tet, respectively. This was achieved by restriction digestion of both plasmids with the enzymes AatII and AhdI sequentially, and then by rendering the cut ends blunt using the enzymes T4 DNA polymerase and the Klenow fragment of DNA polymerase as is well known in the art. The purified fragment containing the majority of the ampicillin resistance gene sequences was removed by agarose gel size exclusion purification electrophoresis, again a technique well known to one skilled in the art. The purified fragment containing Tetr, rop, multiple cloning site and origin of replication, Ori, sequences was relegated reforming a circular plasmid. Tetr is the tetracycline resistance gene,Ori is pUC origin of replication, rop is a deleted part of the rop gene (which mediates RNA I binding to RNA II (Backman, K., Betlach, M., Boyer, H. W. and Yanofsky (1979), Genetic and physical studies on the replication of ColE1-type plasmids, Cold Spring Harbor Symp. Quant. Biol. 43, 69–79). The multiple cloning site or polylinker consists of the following restriction endonuclease enzyme sites: Hind III, SphI, PstI, SalI, XbaI, BamHI.

3. Minimization of lacZ gene sequences in pUC18Tet Amp and pUC19Tet Amp Vectors.

The remaining partially deleted lacZ gene sequences from pUC18 and pUC19 (which in pUC18 and pUC19 code for the α-complementation peptide of -galactosidase) were removed by the following restriction digest reactions: for pUC18Tet Amp, the PstI-BsmbI and BsmbI-BsmbI fragments were removed and the vector realigned. These fragments contained the majority (approximately 420 base pairs) of the remaining lacZ sequences; for pUC19Tet Amp, the EcoRI-BsmbI and BsmbI-BsmbI fragments were removed and the vector realigned. These fragments contained the majority (399 base pairs) of the remaining lacZ sequences.

iii) Polylinker suitable for the insertion of therapeutic genes and regulatory sequences.

Vectors useful according to the invention include a polylinker comprising a variety of restriction sites that are useful in cleaving the vector and incorporating therapeutic genes.

iv) Selective marker gene.

Vectors useful according to the invention may include a gene encoding a selectable marker, e.g., an antibiotic resistance gene such as the bacterial tetracycline resistance gene. Incorporation of the tetracycline resistance gene permits the use of tetracycline as a selective agent in the plasmid preparation procedure according to the invention. One advantage to the use of a tetracycline resistance gene is that tetracycline is not degraded in *E. coli*, as is, for example, ampicillin by the resistance gene -lactamase, and therefore more tetracycline does not have to be added during fermentation. In addition, the tetracycline resistance gene is preferred over a gene encoding ampicillin resistance because tetracycline is prescribed less often as an antibiotic in a clinical setting, and therefore the consequences of readthrough into the antibiotic resistance gene and its expression in the patient be less likely to interfere with the use of an antibiotic in a clinical setting. Likewise, the possibility of spread of antibiotic resistance in the population will be reduced.

v) Absence of other bacterial protein genes.

It is preferred according to the invention that no other bacterial genes are carried on the vector backbone. Absence of other bacterial genes minimizes the possibility of a patient developing an immune response to a foreign gene or its encoded product, where the gene is present and/or expressed in the patient's cells which have been targeted with the therapeutic vector. Other bacterial genes expressed by the host strain during fermentation can result in a metabolic burden on the host which can reduce the biomass and plasmid yields.

vi) Host Cells.

Host cells useful according to the invention may be any bacterial strain, i.e., both Gram positive and Gram negative strains, such as *E. coli* and Salmonella Typhimurium or Bacillus that is capable of maintaining a high copy number of the plasmids described above; for example 20–200 copies. A selection of well established *E. coli* host strains are useful according to the invention and include HB101, DH1, and DH5αF. Strains containing the F plasmid or F plasmid derivatives (for example JM109) are generally not preferred because the F plasmid may co-purify with the therapeutic plasmid product.

EXAMPLE 1

In this example, the pH is determined at which 90–95% plasmid DNA pTX0118 in *E. coli* host strain DH1 is irreversibly denatured, and this pH is correlated with a sodium hydroxide concentration at cell lysis.

The optimum pH and optimum sodium hydroxide concentration at lysis are then identified for pTX0118 purification from host strain DH 1.

Difficulties in measurement of pH in viscous solutions can be overcome by control of pH using varying sodium hydroxide concentrations in the lysis buffer, in other words controlling the pH at lysis by optimizing the sodium hydroxide concentration during cell lysis. *E. coli* strain DH1 cells containing the 13.1 kb sized plasmid pTX0118 were resuspended in 50 mM Tris 10 mM EDTA buffer at pH 8.0 to a cell density of 150 g wet weight/liter. Aliquots of this suspension were lysed in buffer containing 1% sodium dodecyl sulfate (SDS) and a range of sodium hydroxide concentrations from 0.175 to 0.4M (see table below). At each different sodium hydroxide concentration in the lysis buffer, a 2.5 ml sample for DNA purification and a 50 ml sample for pH determination was taken. For all samples 1 volume of resuspended cells was treated with 2 volumes of appropriate lysis buffer.

Plasmid DNA purification and analysis

For the smaller 2.5 ml samples, lysis was carried out for 10 minutes, prior to addition of 1 volume 3M potassium acetate at pH 5.5. Small scale purification of the plasmid was carried out using Qiagen® 500 tips, a commercially available small scale plasmid purification kit supplied by Qiagen Inc. 9600 De Soto Avenue, Chatsworth Calif. 91311, U.S.A., which is supplied with buffers and protocols (Qiagen® Plasmid Handbook, New Edition, February 1995). The protocol was followed from the column equilibration stage (Qiagen® Plasmid Handbook, New Edition, February 1995). The amount of plasmid DNA loaded onto the column was calculated such that it never exceeded 500 μg, the recommended maximum loading for the Qiagen® 500 tip. For the remainder of the procedure, the Qiagen® kit buffers were used throughout. The eluted plasmid DNA was concentrated using propan-2-ol precipitation and centrifugation and the resulting plasmid DNA pellets washed with ethanol, techniques well known in the art and described in Current Protocols in Molecular Biology, ed. F. Ausubel et al., 1995, John Wiley & Sons, Inc. USA, ISBN 0-471-50338-X. Plasmid DNA pellets were then dissolved in 1 ml of 10 mM Tris and 1 mM EDTA at pH 8.0 (TE buffer). A 0.8% agarose gel loaded with 150 ng of each of the samples (except the 0.4M NaOH lysis buffer which had only 150 ng added due to the comparative dilute nature of the recovered plasmid) was run. Electrophoresis was performed at 100V using TAE buffer, techniques well known in the art and described in Current Protocols in Molecular Biology, ed. F. Ausubel et al., 1995, John Wiley & Sons, Inc. U.S.A., ISBN 0-471-50338-X. DNA was visualized by staining with ethidium bromide which fluoresces under ultra violet light. The resultant gel was photographed under ultra violet light (see FIG. 4).

pH determination

In order to eliminate pH heterogeneity caused by high sample viscosity, which may lead to inaccurate determination of the pH at cell lysis, the samples had the viscosity dispersed by using a high shear mixer (Silverson laboratory mixer) two minutes after the addition of the lysis solution. pH measurement was then made using a general purpose laboratory pH electrode and pH meter (see table below).

Results

The table below shows the measured pH values in the samples during lysis.

| Initial concentration of NaOH in lysis buffer | Final concentration of sodium hydroxide At cell lysis (M) | pH after addition of lysis buffer High | pH two minutes later after Shear mixing |
| --- | --- | --- | --- |
| 0.175 | 0.17 | 12.42 | 12.46 |
| 0.185 | 0.123 | 12.43 | 12.47 |
| 0.195 | 0.13 | 12.45 | 12.47 |
| 0.2 | 0.133 | 12.46 | 12.49 |
| 0.4 | 0.266 | 12.64 | 12.64 |

Figure 4:
FIG. 4 is a gel showing bands corresponding to plasmid DNA prepared according to the invention.

FIG. 4 shows an agarose gel loaded with 500 ng of each of the samples except the 0.4M NaOH lysis buffer which had only 150 ng added due to comparative dilute nature of recovered plasmid. Note for the 0.175, 0.185, 0.195 and 0.2M NaOH concentrations there has been comparable plasmid recoveries but for the 0.4M very little plasmid was recovered and what has been recovered has about 50% of the increased mobility irreversibly denatured species. There is also approximately 1–5% of this species present in the 0.2M NaOH sample.

In FIG. 4,

Lane No. 1 corresponds to 1 Kb marker DNA; lane 2, 0.175M Sodium hydroxide lysis buffer sample; lane 3, 0.185M Sodium hydroxide lysis buffer sample; lane 4, 0.195M Sodium hydroxide lysis buffer sample; lane 5, 0.2M Sodium hydroxide lysis buffer sample; lane 6, 0.4M Sodium hydroxide lysis buffer sample.

Conclusions

These results identify the optimum sodium hydroxide concentration in the lysis buffer for this plasmid (vector) and host strain combination as between 0.17 and 0.185M (or 0.113M and 0.123M final concentration during cell lysis) because this is the sodium hydroxide range 0.015 to 0.03M below the concentration in which approximately 1–5% denatured plasmid is visualized (0.2M, lane 5, see FIG. 4). Agarose gel electrophoresis identified no visible band of irreversibly denatured species in the 0.0175 to 0.185M sodium hydroxide range. This range correlates to approximately 0.17 pH units below the pH value at which 50% of the plasmid DNA visualized by agarose gel electrophoresis was irreversibly denatured (which, in turn corresponds to approximately 90–95% irreversibly denatured DNA when the irretrievable plasmid DNA not recovered has been taken into consideration).

EXAMPLE 2

In this example, the plasmid preparation process described in Example 1 is repeated using the sodium hydroxide titration to identify the optimum concentration at cell lysis for *E. coli* DH1 cells containing plasmid pTX0118.

Cell pellets collected from *E. coli* strain DH1 cells containing the plasmid pTX0118 grown in flasks were thawed and re-suspended at 150 g/liter in 50 mM Tris 10 mM EDTA pH8 containing 100 g/ml RNAase A as described above and were kept on ice for 30 minutes. 2 ml aliquots of the cell suspension were then lysed with 2 volumes of 1% SDS solution containing the following concentrations of sodium hydroxide solution

| Concentration of Sodium hydroxide in lysis buffer | Final sodium hydroxide concentration at cell lysis |
| --- | --- |
| 0.16M | 0.107M |
| 0.17M | 0.113M |
| 0.18M | 0.12M |
| 0.19M | 0.127M |
| 0.2M | 0.133M |
| 0.2M ( Qiagen ® buffer) | 0.133M |

After 10 minutes lysis, 1 volume of 3M potassium acetate was added. Samples were then centrifuged ( Sorvall RT6000D centrifuge with swing out H1000A rotor, 3.5K rpm 35 minutes) and supernatants loaded onto Qiagen® 500 tips as previously described. Plasmid DNA was concentration using propan-2-ol precipitation and ethanol washing as described above.

Pellets of plasmid DNA were dissolved in 0.5 ml TE buffer. 500 ng of each sample were digested (cut) with the restriction enzyme Cla1 (New England Biolabs (U.K.), Ltd. 67 Knowl Piece, Wilbury Way, Hitchin, Hertfordshire SG4 0TY, U.K.) using methods similar to those described herein.

Figure 5:
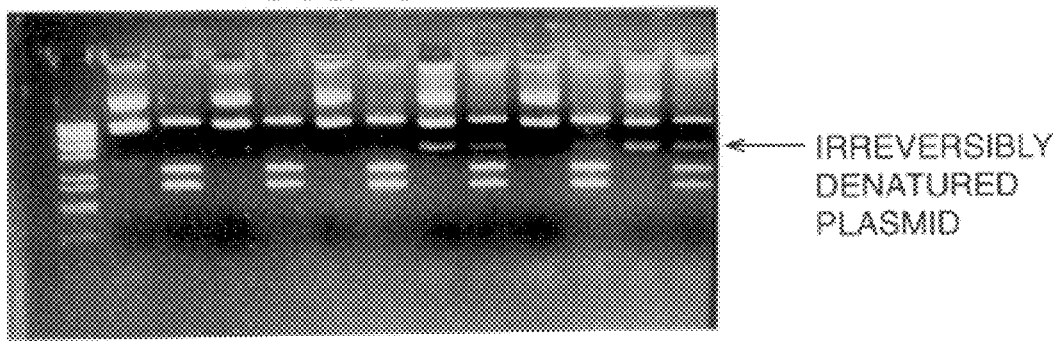
FIG. 5 is a gel showing bands corresponding to plasmid DNA prepared according to the invention.

FIG. 5 shows cut and uncut samples of each. Note in Lane 8 (0.19M sodium hydroxide in the lysis buffer) that approximately 5% of the plasmid DNA appears as a higher mobility band which is also present in the digested sample, i.e. irreversibly denatured. This band is also present in 0.2M sodium hydroxide lysis buffer sample and Qiagen® P2 lysis buffer. This band is not apparent in the 0.16, 0.17 or 17 or 0.18M sodium hydroxide lysis buffers.

| In FIG. 5, Lane No | Sample |
| --- | --- |
| 1 | BstII lambda marker |
| 2 | 0.16M NaOH lysis buffer sample Uncut |
| 3 | 0.16M NaOH lysis buffer sample Cla1 digested |
| 4 | 0.17M NaOH lysis buffer sample Uncut |
| 5 | 0.17M NaOH lysis buffer sample Cla1 digested |
| 6 | 0.18M NaOH lysis buffer sample Uncut |
| 7 | 0.18M NaOH lysis buffer sample Cla1 digested |
| 8 | 0.19M NaOH lysis buffer sample Uncut |
| 9 | 0.19M NaOH lysis buffer sample Cla1 digested |
| 10 | 0.20M NaOH lysis buffer sample Uncut |
| 11 | 0.20M NaOH lysis buffer sample Cla1 digested |
| 12 | Qiagen ® P2 Uncut |
| 13 | Qiagen ® P2 Cla1 digested |

Conclusion

In this experiment, for this plasmid and host strain combination the formation of a visible band corresponding to increased-mobility irreversibly denatured plasmid DNA can be prevented by using a sodium hydroxide concentration in the lysis buffer of between 0.16M and 0.175M in 1% SDS (or a NaOH concentration at lysis t lysis of 0.107 and 0.117M). This overlaps with the 0.17 to 0.185M NaOH concentration range in lysis buffer that was identified in the previous example for the same host vector combination. Therefore the NaOH concentration chosen for the large scale preparation of this plasmid was 0.175M, in the overlapping range covered by both experiments.

EXAMPLE 3

Large scale plasmid DNA production from *E. coli* strain DH1 containing plasmid pTX0118 employing cell lysis at the optimum sodium hydroxide concentration according to the invention.

Cell Growth in Culture

An alternative batch fermentation medium highly enriched with nucleic acid synthesis precursors to maximize plasmid yield and quality useful according to the invention was used for this example, as detailed below.

i) Inoculation

E. coli DH1 cells transformed with plasmid pTX0118 were recovered from cryopreserved stocks (exponential growth phase cells snap frozen in LB medium supplemented with 20% sterile glycerol as a cryoprotectant) and streaked onto LBtet plates containing LB medium (10 g/l bacto tryptone, 5 g/l yeast extract and 5 g/l sodium chloride. The pH was adjusted to pH 7 by the addition of 1M sodium hydroxide), 12 g/ml tetracycline and 1.2% agar. Six single colonies from the plate were inoculated each into 20 ml of LB medium supplemented with 12 mg/ml tetracycline in separate sterile plastic Erlenmeyer flasks and grown for 12–16 hours at 37° and 200 rpm in a shaking incubator. One of these cultures was then used to inoculate 200 ml of sterile LB medium supplemented with 12 g/ml tetracycline in a 2 L Erlenmeyer flasks. This was grown at 37° C. and 200 rpm in a shaking incubator and used to inoculate two 5 L Erlenmeyer flasks each containing 1000 ml of sterile modified TB medium (11.8 g/l bacto tryptone, 23.6 g/l yeast extract, 2.2 g/l KH2PO4 and 9.4 g/l KH2PO4. The pH is adjusted to pH 7 by the addition of 1M sodium hydroxide) supplemented with 12 g/ml tetracycline. These were grown at 30° C. and 200 rpm in a shaking incubator and used to inoculate the fermenter vessel when in mid-exponential phase, after 5 hours and at an OD600 nm of 2 units.

ii) Fermentation

The fermenter vessel used was a 50 L working volume Life Sciences Laboratories Ltd. 50/75LP stirred tank bioreactor prepared as follows:

a) batch medium (in 46L) sterilized at 120° C. for 30 minutes in the fermenter vessel

| Component | Quantity Required |
|---|---|
| Potassium dihydrogen phosphate (KH2PO4) | 150 g |
| Disodium hydrogen phosphate (Na2HPO4) | 300 g |
| Sodium chloride (NaCl) | 25 g |
| Gibco Select Peptone 140 | 100 g |
| Ammonium sulphate (NH4)2SO4 | 500 g |
| Trace Elements Solution (see below for composition) | 25 ml |
| BDH Polypropylene Glycol (Molecular Weight 2025) | 100 ml |
| Calcium chloride dihydrate (CaCl22H2O) | 1.5 g |
| Iron (Ferrous) sulphate heptahydrate (FeSO4 7H2O) | 2 g |
| Citric Acid | 1 g |
| Gibco Select Yeast Extract | 1000 g |
| Deionized Water | 46000 ml |

TRACE ELEMENT SOLUTION PREPARATION

| Component | Quantity Required |
|---|---|
| Cobalt chloride hexahydrate (CoCl2 6H2O) | 2 g |
| Copper (II) chloride dihydrate (CuCl2 2H2O) | 1.9 g |
| Boric acid (H3 BO3) | 1.6 g |
| Manganese sulphate monohydrate (MnSO4 H2O) | 1.6 g |
| Sodium molybdate dihydrate (Na2MoO42H2O) | 2 g |
| Zinc chloride heptahydrate (ZnCl2 7H2O) | 2 g |
| Ferric Sulphate (Fe2(SO4)3.xH2O | 1 g |
| Calcium Chloride dihydrate (CaCl2.2H2O) | 1 g |
| Citric Acid | 60 g |
| Deionized water | to 1000 ml | b) sterilized separately by autoclaving (121° C. for 15 minutes) for post sterilization addition (psa) to the vessel

PSA SOLUTION 1 PREPARATION

| Component | Quantity Required |
|---|---|
| Magnesium sulphate heptahydrate (MgSO4 7H2O) | 25 g |
| Deionized water | 600 ml |

Prepare and sterilize by autoclaving at 121° C. for 15 minutes for addition to the autoclaved fermenter vessel.

PSA SOLUTION 2 PREPARATION

| Component | Quantity Required |
|---|---|
| BDH Glycerol | 1400 ml |

Prepare and sterilize by autoclaving at 121° C. for 15 minutes for addition to the autoclaved fermenter vessel.

c) 0.2 mm filter sterilized for psa directly into the fermenter vessel.

PSA SOLUTION 3 PREPARATION

| Component | Quantity Required |
|---|---|
| Thiamine Hydrochloride | 0.4 g |
| Tetracycline hydrochloride | 400 mg |
| Vitamins solution (V1) (See below for composition) | 25 ml |

Prepare and filter sterilize directly into the autoclaved fermenter vessel.

VITAMIN SOLUTION (V1) PREPARATION

| Component | Quantity Required |
|---|---|
| Biotin | 0.06 |
| Folic acid | 0.04 |
| Pyridoxine-HCl | 1.4 |
| Riboflavin | 0.42 |
| Pantothenoic acid | 5.4 |
| Niacin | 6.1 |
| Deionized water | 1000 ml |

Fermentation

Batch fermentation was carried out at 3° C. and pH 6.8. The pH was controlled by the automatic addition of 4M NaOH and 2.5M H2SO4. The dissolved oxygen (DO) setpoint was 50% of saturation and was controlled by the automatic adjustment of the fermenter agitation speed. Maximum agitation speed was 1200 rpm. Air supply was manually adjusted between 1 and 4 air volumes/fermenter volume/minute to maintain the DO at 50% of saturation once the agitation speed had reached its maximum. Throughout the fermentation, samples were taken for measurement of optical density (OD600 nm). Cell pellets from each sample were collected by centrifugation and stored at −20° C. for subsequent analysis of plasmid yield (using the Qiagen® 500 tip protocol as described earlier) and dry weight determination (briefly, the dry cell weight of cells pellets collected by centrifugation from a known volume of fermenter culture was determined after drying to equilibrium at 85° C.).

Fermentation was continued until the OD600 nm reached 25 units or a dry cell weight of approximately 12 g/l. The vessel contents was then cooled to 10° C., emptied into 1000 ml sealable centrifuge bottles and the cells collected by centrifugation at 4500 rpm in a Sorvall RC3B plus centrifuge in a H6000A rotor.

The supernatant was decanted and disinfected before being discarded and the cell pellets weighed (wet weight) and frozen at −80° C. The frozen cells were processed as follows:

Preparation of a Cell Suspension 1200 g (wet weight) of cells were removed from the −80° C. Freezer and thawed at 18° C. for 1 hour. Cell suspension buffer (50 mM Tris 10 mM EDTA at pH 8.0) was added to each centrifuge bottle sufficient to solubilize the cell pellet. A Pallet knife was used to gently assist cell suspension. The resuspended cells were pooled and the volume adjusted with cell suspension buffer to give a final cell concentration of 150 g cells (wet weight)/ liter of cell suspension buffer.

Cell Lysis

The cell suspension was aliquotted into 4×2 L units in clean stainless steel cans. Molecular biology grade bovine RNAaseA (Sigma Aldrich Company LTD., Fancy Road, Poole, Dorset BH12 4QH, U.K.) was added at a final concentration of 100 mg/liter of cell suspension.

4 L of lysis buffer containing 0.175M NaOH and 1% SDS at 18–22° C. was added to each 2 L aliquot of cell suspension, mixed gently with a large stainless steel spoon and incubated at 18–22° C. for 10 minutes.

After this 10 minute incubation, 2 L of 3M potassium acetate with 10 mM EDTA at pH 5.5 was poured into each can.

The contents of all four cans was pooled into two 20 L stainless steel holding vessels and held at 18–22° C. for 1 hr.

Filtration

The contents of the two holding vessels was transfered by pumping through a 100 μm and 25 μm woven nylon bag filters in 7 inch diameter stainless steel filter housings (Plastok Ltd. 79 Market Street, Birkenhead, Wirral, Merseyside L41 6AN, U.K.) in series.

The filtrate was collected into two 20 L stainless steel Holding tanks. Bovine RNAaseA is added as before to a final concentration of 66–80 mg/L.

Expanded Bed Chromatography 7.5 L of DEAE Streamline (Pharmacia) media was decanted into a Streamline 200 chromatography column (Pharmacia). The chromatography bed was expanded in an upward flow mode and washed with 0.1M NaOH before equilibration in 0.8M KAc, 10 mM EDTA pH 5.5 as is well known to one skilled in the art.

With the column bed still expanded, the filtrate from above was pumped (loaded) onto the column. Once loaded, the column was washed with 0.8M potassium acetate (KAc), 10 mM EDTA pH 5.5 (equilibration buffer), then washed with 25 mM KAc, 10 mM EDTA at pH 5.5 until the on-line absorbance detector (optical density at 254 nm or OD254 nm) was reduced from the maximum OD254 nm value to 50% or less.

At this point the fluid flow direction was reversed using downward flow and the head lowered to pack the chromatography column into conventional axial operation.

The column is then washed to within about 5% of the maximum OD254 nm value of with 25 mM KAc 10 mM EDTA pH 5.5. Following this a 0.5M NaCl, 25 mM KAc 10 mM EDTA pH 5.5 wash is used to remove the bulk of the RNA and RNA fragments bound to the column matrix. Washing is continued until the OD254 nm value has been reduced to 10% or less of the maximum OD254 nm value.

Plasmid DNA is then eluted with 0.75M NaCl, 25mM KAc 10 mM EDTA pH 5.5. The eluted product is stored at +4 to +8° C.

Concentration of Streamline Eluate

An Amicon CH2 ultrafiltration device was then washed using 0.1M NaOH and equilibrated in 0.75M NaCl, 25 mM KAc 10 mM EDTA at pH 5.5. The eluate was concentrated to approximately 400 ml final volume by ultrafiltration using an SIY-30 Kilodalton molecular weight cut off membrane. The concentrate was removed and decanted into a sterile bottle. Residual plasmid DNA was washed out of the CH2 cartridge with approximately 400 ml of 0.75M NaCl, 25 mM KAc 10 mM EDTA pH 5.5 buffer and pooled with the concentrate. This was stored at 4–10° C.

S500 Gel Permeation Chromatography

An Amicon VS130 column containing a 56 cm bed of Pharmacia S500HR gel was sanitized and equilibrated in 0.3M NaCl in water for injection. The fraction collector was set up and checked according to the manufacturer's instructions. The concentrate from above was loaded onto the column and the flow through monitored at OD254 nm. When the OD254 nm. rises (the beginning of a 'peak'), fractions (approximately 200 ml) each are collected throughout the peaks. From the first eluted peak, OD measurement are made on each peak fraction and ones with significant OD254 nm., which contain plasmid DNA are pooled. Pooled fractions are stored frozen at −80° C.

Analysis and Results

A sample of the frozen plasmid DNA pooled fractions from above is analyzed for

Appearance: Clear, colorless solution

Form: Percentage closed circular 99.2, open circular form 12.5 as determined by gel electrophoresis. (See FIG. 6)

Stability: Size and restriction pattern consistent with original construct.

E. coli chromosomal DNA: Less than 5% contaminating chromosomal DNA as judged by PCR assay.

RNA: Not detectable as determined by agarose gel electrophoresis.

Endotoxin: 3.5 EU/mg plasmid DNA.

Protein: Not detectable when determined by silver stained sodium dodecyl sulfate polyacrylamide gel electrophoresis (SDS PAGE).

Figure 6:
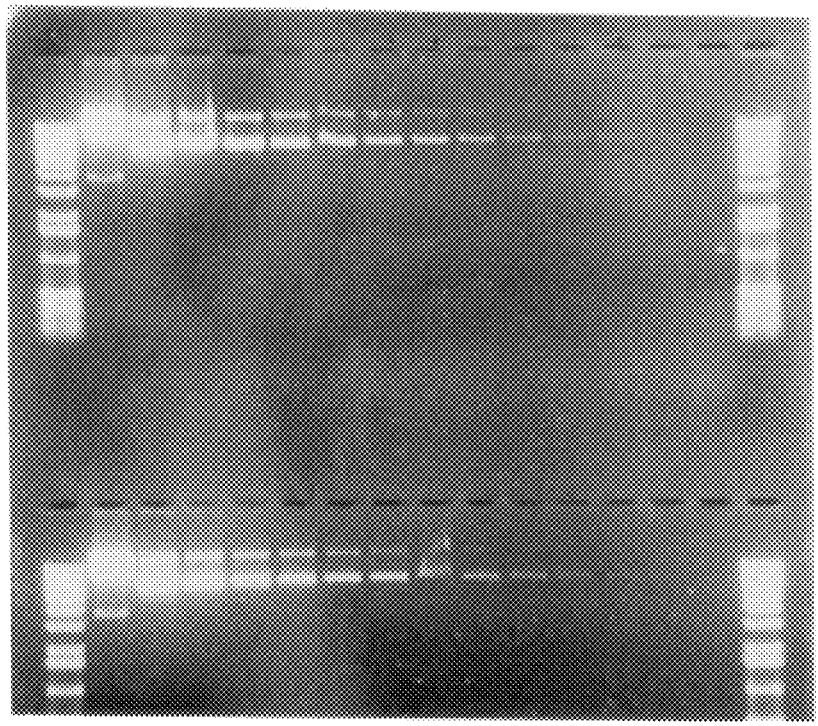
FIG. 6 is a gel showing bands corresponding to plasmid DNA prepared according to the invention.

FIG. 6 shows purity of large scale production of batch of pTX0118.

| Lane | Sample |
| --- | --- |
| 1 | 1 kb ladder |
| 2 | Tox 2.1 internal plasmid marker |
| 3 | Large scale final product 1000 ng |
| 4 | Large scale final product 500 ng |
| 5 | Large scale final product 250 ng |
| 6 | Large scale final product 125 ng |
| 7 | Large scale final product 62.5 ng |
| 8 | Large scale final product 31.25 ng |
| 9 | Large scale final product 16 ng |
| 10 | Large scale final product 8 ng |
| 11 | Large scale final product 4 ng |
| 12 | Large scale final product 2 ng |
| 13 | Large scale final product 1 ng |
| 14 | Large scale final product 0.5 ng |
| 15 | load buffer |
| 16 | 1 kb ladder |

Discussion and Conclusions

The purity of the plasmid produced in this example of a large scale procedure employing the combination of large scale controlled lysis conditions and scalable purification methodologies such as Streamline DEAE fluidized bed chromatography is higher than plasmid DNA purified by other techniques well known in the art. For example in this case the resulting endotoxin in content is 3.5 EU/mg. The endotoxin contents of purified plasmid using a Biowhittaker taker KQC1 assay are as follows: for pTX0118 from a large-scale preparation, 3.5 EU/mg (assay carried out at 14.3 µg/ml; pTX0118 DNA purified by single CsCl/EtBr equilibrium centrifugation (as described herein) >2500 EU/mg (at 20 µg/ml). The plasmid was derived in the latter case from a flask culture of the same stock of bacterial cells, E. coli DH1. The method used for this process is well known in the art (as described in Current Protocols in Molecular Biology, ed. F. Ausubel et al., 1995, John Wiley & Sons, Inc. U.S.A., ISBN 0-471-50338-X). In this example the endotoxin content of caesium chloride purified DNA was in excess of 2500 EU/mg DNA. Other methodologies such as Qiagen® Ultrapure 100 anion exchange columns employ buffers such as the Qiagen® Endotoxin Removal Buffer to achieve in levels of about 50 EU/mg DNA (J. Schorr, P. Moritz, T. Seddon and M. Schleef, New York Academy of Sciences 772, p271 Nov. 27, 1995; PCT WO 95/21177 and PCT WO 95/21179). Such buffers contain potentially toxic detergent, the use of which is undesirable at this stage in the production of pharmaceutical grade DNA.

In this example the use of toxic agents such as caesium chloride and ethidium bromide or use of other agents whose suitability in pharmaceutical production and applications is unknown, to be avoided, undesirable or unacceptable was not required to achieve levels of endotoxin, and RNA as low as or lower than in the prior art (J. Schorr, P. Moritz, T. Seddon and M. Schleef, New York Academy of Sciences 772, p271 Nov. 27, 1995).

EXAMPLE 4

Use of different sodium hydroxide concentrations to control irreversible denaturation during the purification of plasmid from E. Coli DH1 cells containing plasmid pTX0161.

Frozen E. coli cells containing the 7.7 kb plasmid pTX0161 from a 5l fermentation were thawed and resuspended at 150 g/l wet weight in 50 mM Tris, 10 mM EDTA at pH 8.0 containing 100 g/ml RNAase A (Sigma-Aldrich Company LTD., Fancy Road, Poole, Dorset BH12 4QH, U.K.). Lysis was carried out using a 1:2 volume ratio of cell suspension to lysis buffer. Lysis reaction time was for 10 minutes with lysis buffer containing 1% SDS and 0.175, 0.18, 0.19 or 0.2M sodium hydroxide. 1 volume of 3M potassium acetate at pH 5.5 was then added to each, mixed, and samples spun at 13K rpm for 30 minutes in a Sorvall RC5B plus centrifuge fitted with a SS34 rotor. The supernatants were then loaded onto Qiagen® 500 tips for purification as above. Purified DNA from each Qiagen 500 tips was eluted, concentrated as above and dissolved in 1 ml TE buffer.

Figure 7:
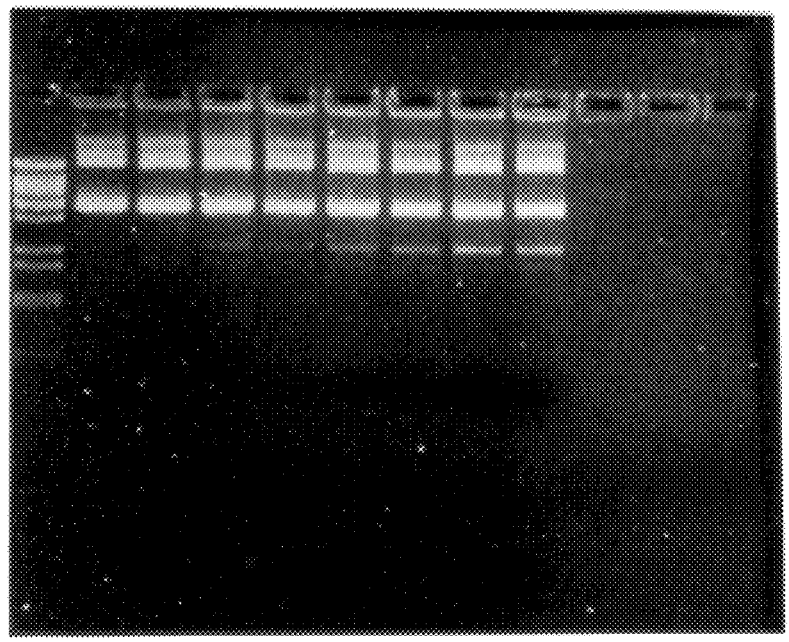
FIG. 7 is a gel showing bands corresponding to plasmid DNA prepared according to the invention.

FIG. 7 shows a photograph of an 0.8% agarose gel taken after agarose gel electrophoresis of all the samples had been performed. In the 0.175M NaOH lysis buffer treated sample there is no visible band corresponding to higher mobility irreversibly denatured plasmid DNA. Approximately 1–5% can be seen in 0.18M lysis buffer treated sample and >5% can be seen in the 0.19M and 0.2M NaOH lysis buffer treated samples.

FIG. 7

| Lane No. | Sample |
| --- | --- |
| 1 | lambda BstII marker |
| 2 | 0.175M NaOH lysis buffer sample |
| 3 | 0.175M NaOH lysis buffer sample |
| 4 | 0.18M NaOH lysis buffer sample |
| 5 | 0.18M NaOH lysis buffer sample |
| 6 | 0.19M NaOH lysis buffer sample |
| 7 | 0.19M NaOH lysis buffer sample |
| 8 | 0.20M NaOH lysis buffer sample |
| 9 | 0.20M NaOH lysis buffer sample |

Figure 8:
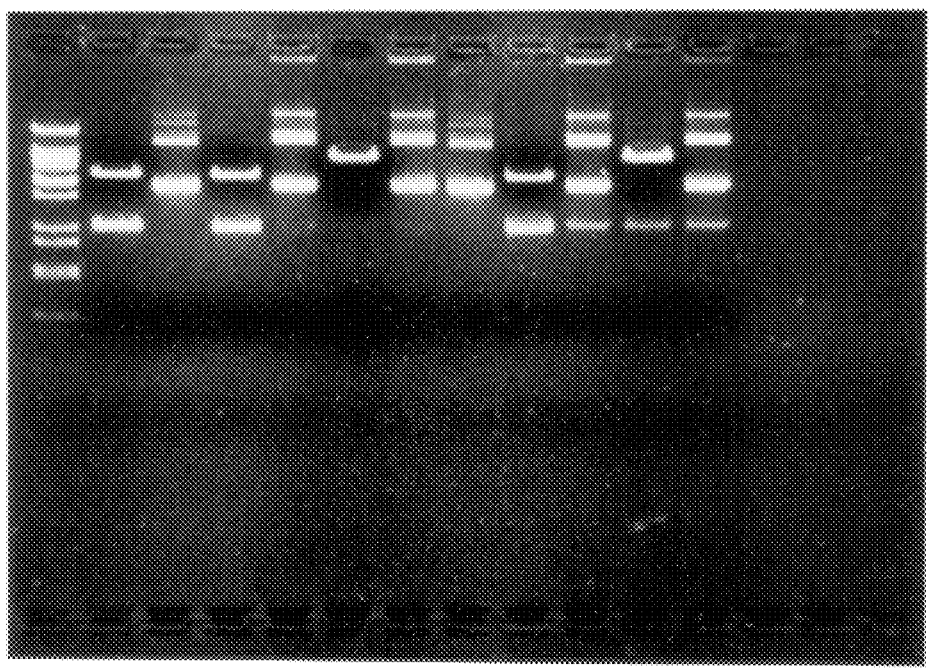
FIG. 8 is a gel of restriction enzyme digests of plasmid pTX0161

FIG. 8 shows restriction endonuclease enzyme digests of two of the samples, the 0.175M NaOH lysis buffer and the 0.2M NaOH lysis buffer treated samples. 300 ng of these two samples were digested with two restriction enzymes; EcoRV and Xba I (obtained from the (New England Biolabs (U.K.), Ltd. 67 Knowl Piece, Wilbury Way, Hitchin, Hertfordshire SG4 OTY, U.K.) in separate reactions used at between 40 and 67 units g plasmid DNA for 1.75 hours under the conditions recommended by the supplier. Plasmid DNA prepared by caesium chloride/ethidium bromide equilibrium centrifugation (as described in Current Protocols in Molecular Biology, ed. F. Ausubel et al., 1995, John Wiley & Sons, Inc. U.S.A., ISBN 0-471-50338-X) was also digested under the same conditions as a control. The control plasmid DNA is prepared in such a way that high mobility irreversibly denatured DNA will not contaminate the sample. In Lane 11, the band which present in the Xba1 digested plasmid DNA from the 0.2M NaOH lysis buffer treated sample is also present in the undigested sample. This demonstrated irreversibly denatured plasmid DNA cannot be digested by Xbal under these conditions.

FIG. 8 is a restriction digest of plasmid pTX0161

| Lane No. | Sample |
| --- | --- |
| 1 | lambda BstII marker |
| 2 | pTX0161 Caesium purified EcoRV digested |
| 3 | pTX0161 Caesium Uncut |
| 4 | 0.175M NaOH Lysis buffer sample Eco RV digested |
| 5 | 0.175M NaOH Lysis Uncut |
| 6 | 0.175M NaOH Lysis Xbal digested |
| 7 | 0.175M NaOH Lysis Uncut |
| 8 | pTX0161 Caesium purified Uncut |
| 9 | 0.2M NaOH Lysis buffer sample EcoRV digested |
| 10 | 0.2M NaOH Lysis buffer Uncut |

-continued

| Lane No. | Sample |
|---|---|
| 11 | 0.2M NaOH Lysis buffer XbaI digested |
| 12 | 0.2M NaOH Lysis buffer Uncut |

The irreversibly denatured plasmid DNA band is present in Lane 10 (undigested) but is masked in Lane 9 (EcoRV digested) by an EcoRV digestion fragment which has the same mobility. None of these bands are visible in the 0.175M NaOH lysis buffer treated sample.

Conclusions

The optimum lysis buffer sodium hydroxide concentration to treat *E. coli* DH1 cells containing plasmid pTX0161 is 0.15 to 0.165M (corresponding to an optimum NaOH concentration at lysis of 0.1 to 0.11M). This optimum range is lower than optimum ranges found for different plasmid/host cell combinations, thus further demonstrating the benefit of the inventive methods for identifying an optimum lysis range for each different plasmid or plasmid host strain combination.

This experiment also demonstrated that the irreversibly denatured plasmid DNA is denatured irreversibly to the extent that it could not be digested by EcoRV or XbaI, and therefore, is unlikely to be digestible by other restriction endonucleases, under the conditions used here.

EXAMPLE 5

Another example of control of sodium hydroxide concentration in the lysis mix to prevent formation of denatured plasmid In another experiment the 8 kb plasmid pSW1 (also known as pTX0100) containing *E. coli* DH1 cells, were grown in Erlenmeyer flasks containing LB medium supplemented with 12 mg/l tetracycline to stationary phase. Cells were harvested as pellets after centrifugation at 3500 rpm in a Sorval RT000D centrifuge in a H1000B rotor. The supernatant was discarded and the cell pellets frozen at –20° C.

Subsequently cells were thawed at room temperature (8–22° C.) for approximately 1 hour. The thawed cells were then resuspended in 50 mm Tris, 10 mm EDTA at pH 8.0 and RNAase A added to 100 g/ml. 2.5 ml aliquots of the cell suspension were then mixed with 2 volumes of the following concentrations of sodium hydroxide in 1% SDS lysis buffer:
0.15M
0.16M
0.17M
0.18M
19M
2M After 5 minutes 1 volume of 3M potassium acetate at pH 5.5 was added to each, held on ice for minutes, then the solution clarified by centrifugation (Sorvall SS34 rotor 1300 rpm for 30 minutes). The supernatants from each were applied to Qiagen® 500 tips and purified as in the previous examples and concentrated using IPA precipitation then ethanol washing as before. Plasmid DNA purified was dissolved in TE buffer and 500 ng of each sample loaded on a 0.8% agarose gel.

Figure 9:
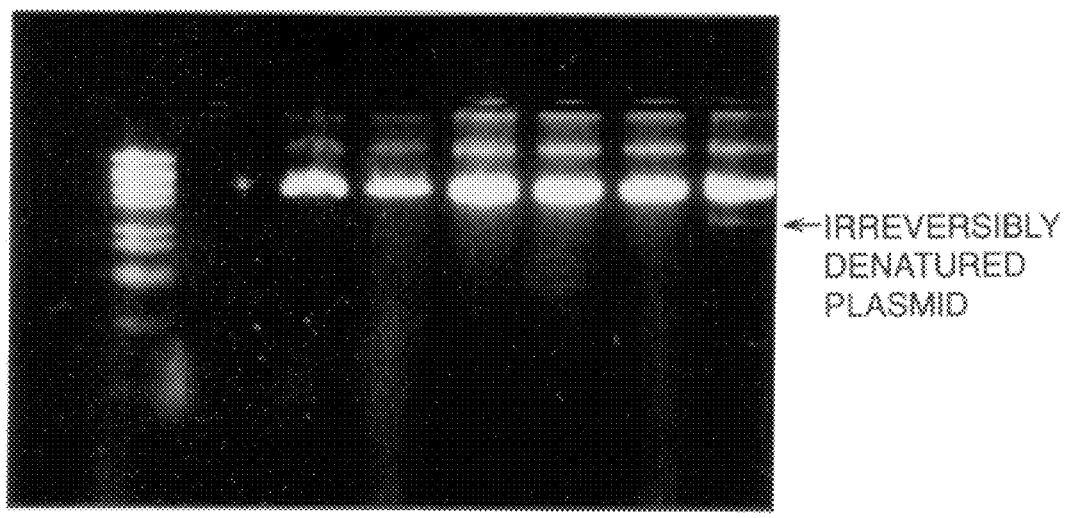
FIG. 9 is a gel showing bands corresponding to plasmid DNA prepared according to the invention.

FIG. 9 shows the appearance of approximately 5% denatured plasmid DNA as the increased mobility irreversibly denatured band running ahead of the main supercoiled band in the 0.2M NaOH/1% SDS Lane (Lane 8).

FIG. 9

| Lane No | Sample |
|---|---|
| 1 | Lambda BstII marker |
| 2 | — |
| 3 | 0.15M NaOH in lysis buffer |
| 4 | 0.16M NaOH in lysis buffer |
| 5 | 0.17M NaOH in lysis buffer |
| 6 | 0.18M NaOH in lysis buffer |
| 7 | 0.19M NaOH in lysis buffer |
| 8 | 0.2M NaOH in lysis buffer |

Conclusion

For this particular plasmid and host strain combination the use of two volumes of lysis buffer containing between 0.17M and 0.185M NaOH in 1% SDS solution (or 0.11M to 0.123M NaOH at cell lysis) results in plasmid which is free of the increased mobility irreversibly denature species. Again this is different than the earlier examples, this plasmid being recovered without denaturation from cell lysis in a higher NaOH concentration range, as predicted according to the inventive methods.

EXAMPLE 6

Experiment demonstrating that use of the optimum sodium hydroxide concentration at cell lysis allows potential to increase lysis times Frozen cell paste from 50 liter fermentation (performed as described above) of *E. coli* strain DH1 cells containing the 17 kb plasmid pTX0201 was thawed at room temperature then resuspended to 150 g/l wet weight as in the previous experiments. 2.5 ml aliquots of the cell suspension were treated with 2 volumes of the appropriate lysis buffer. In this experiment a more narrow range of lysis solutions were used i.e. 0.17M, 0.18, 0.19 and 0.2M NaOH, all in 1% SDS solution. In this experiment triplicates of the 0.17M and 0.18M NaOH lysis buffers were carried out so that different lysis times could be tested. For the 0.17M and 0.18M NaOH lysis buffer samples the lysis times were 5 minutes, 10 minutes and 15 minutes. For the 0.19 and 0.2M NaOH lysis buffers the lysis time was 5 minutes. Neutralization followed the relevant lysis time using 1 volume of 3M potassium acetate (KAc) at pH 5.5. After centrifugation (Sorvall SS34 rotor 14000 rpm 30 mins) the supernatants were purified using Qiagen® 500 tips as previously described. The eluted plasmid was concentrated using propan-2-ol (IPA) precipitation, the pellets washed with ethanol and then the DNA dissolved in 0.5 ml TE. 500 ng of each sample was loaded on an agarose gel.

Figure 10:
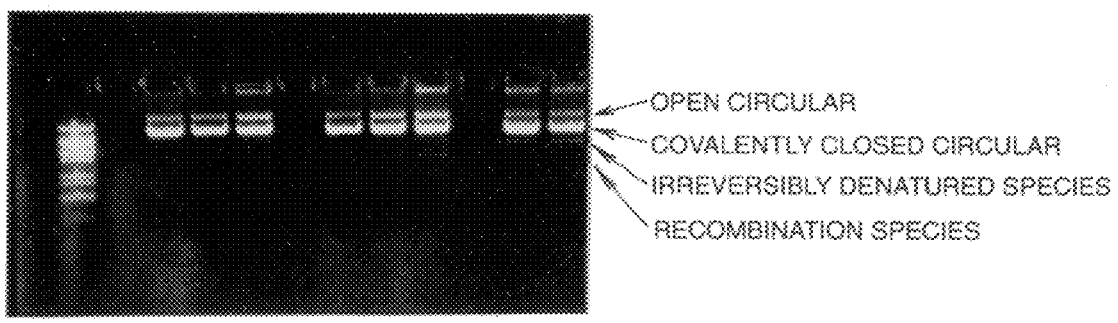
FIG. 10 is a gel showing bands corresponding to plasmid DNA prepared according to the invention.

FIG. 10 Note in all lanes the appearance of a smaller plasmid band. This is a characterized smaller plasmid caused by re-arrangement of the pTX0201 plasmid known to occur during fermentation. In addition, the increased mobility irreversibly denatured species as shown in FIG. 10 can be clearly seen in 0.19M and 0.2M NaOH lysis buffer treated samples (lanes 11 and 12) at approximately 1–5%. There is no visible increased mobility irreversibly denatured band in any of the 0.17M or 0.18M NaOH lysis buffer examples despite the increase in lysis time to 15 minutes.

FIG. 10 shows results from differing lysis times at different NaOH concentrations.

| Lane | Sample |
|---|---|
| 1 | lambda BstII marker |
| 2 | — |
| 3 | 0.17M NaOH lysis buffer 5 minute lysis time |
| 4 | 0.17M NaOH lysis buffer 10 minute lysis time |
| 5 | 0.17M NaOH lysis buffer 15 minute lysis time |
| 6 | — |
| 7 | 0.18M NaOH lysis buffer 5 minute lysis time |
| 8 | 0.18M NaOH lysis buffer 10 minute lysis time |
| 9 | 0.18M NaOH lysis buffer 15 minute lysis time |
| 10 | — |
| 11 | 0.19M NaOH lysis buffer 5 minute lysis time |
| 12 | 0.20M NaOH lysis buffer 5 minute lysis time |

Conclusions

As predicted according to the inventive methods, use of lower concentrations of the sodium hydroxide in the lysis buffer is herein demonstrated that it is possible to increase the lysis time without the formation of irreversibly denatured plasmid DNA. In this case it was possible to use. 0.17M NaOH (in the range 0.016 to 0.175M as defined according to the invention at 0.015 to 0.03M below the sodium hydroxide concentration in which approximately 5% plasmid denaturation is seen) in the lysis buffer in ratios of 1:2 with the resuspended cells and continue the lysis for up to 15 minutes without detrimental effects on the plasmid quality. This may be advantages to the overall quality of the plasmid preparation. For example increased contact with agents, for example sodium hydroxide, in the lysis buffer known to reduce, remove or destroy contaminants, for example endotoxin. Sodium hydroxide treatment, usually at 0.1M to 0.5M, is a recognized method used in the pharmaceutical industry for destruction of endotoxin.

EXAMPLE 7

Experiment showing irreversible plasmid DNA formation leads to irretrievable plasmid DNA and lower plasmid DNA yields Frozen cells from a fermentation of *E. coli* strain DH1 cells containing the 8 kb plasmid pSW1 (also known as pTX0100) were thawed and then resuspended at a concentration of 150 g/l wet weight using 50 mm Tris, 10 mm EDTA pH 8 containing 100 mg/ml RNAase A as described above. Three 5 ml aliquots of this cell suspension were treated with 2 volumes of 3 different lysis buffers (1=0.2M NaOH in 1% SDS, 2=0.175M NaOH in 1% SDS and 3=0.15M NaOH in 1% SDS). Cells were mixed gently and left for 5 minutes prior to addition of I volume 5M KAc at pH 5.5. The resulting precipitate was left on ice for at least 10 minutes prior to centrifugation at 12000 rpm (Sorvall SS34 rotor) for 30 minutes. All three samples were purified using Qiagen® 500 tips as described earlier. The eluted plasmids were then concentrated by IPA precipitation and ethanol washing as before. The pellets were dissolved in 0.5 ml TE buffer, prior to analysis. The yields from the three samples were compared by performing 1/10 dilutions in TE buffer, then using the dilutions for 230 nm–350 nm absorbance scans using a Philips 8700 series spectrophotometer. Absorbance at 254 nm is used to calculate plasmid DNA concentration and yield.

| Concentration of sodium hydroxide in lysis buffer, M | Overall NaOH concentration at lysis in M | µG plasmid recovered |
|---|---|---|
| 0.15 | 0.1 | 341 |
| 0.175 | 0.117 | 502 |
| 0.2 | 0.133 | 26 |

Figure 11:
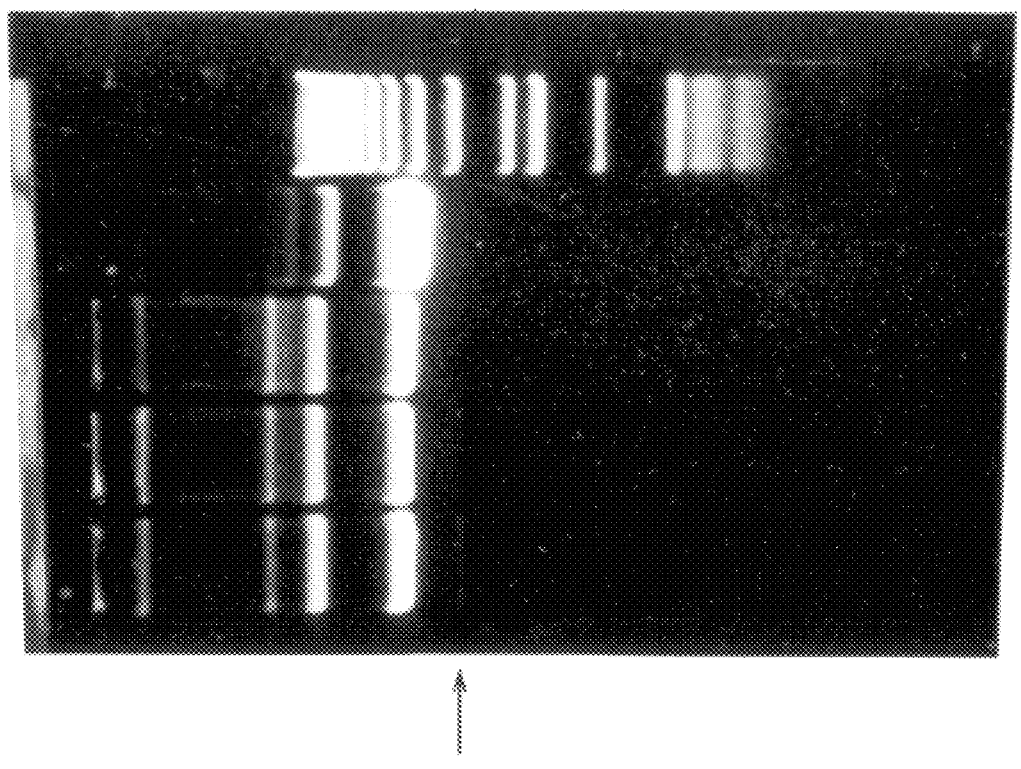
FIG. 11 is a gel showing bands corresponding to plasmid DNA prepared according to the invention.
Figure 12:
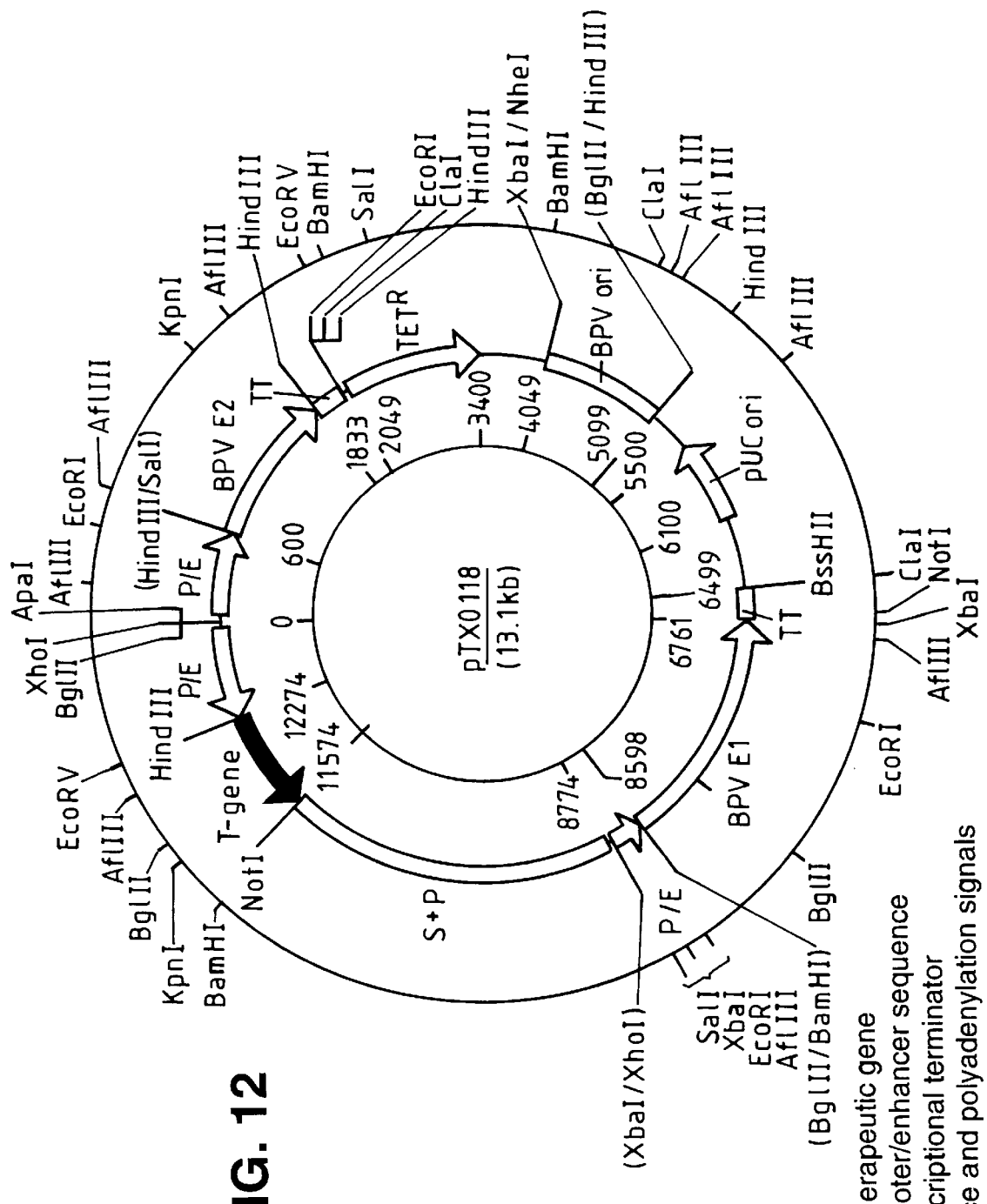
FIG. 12 is a plasmid map of pTX0118.
Figure 13:
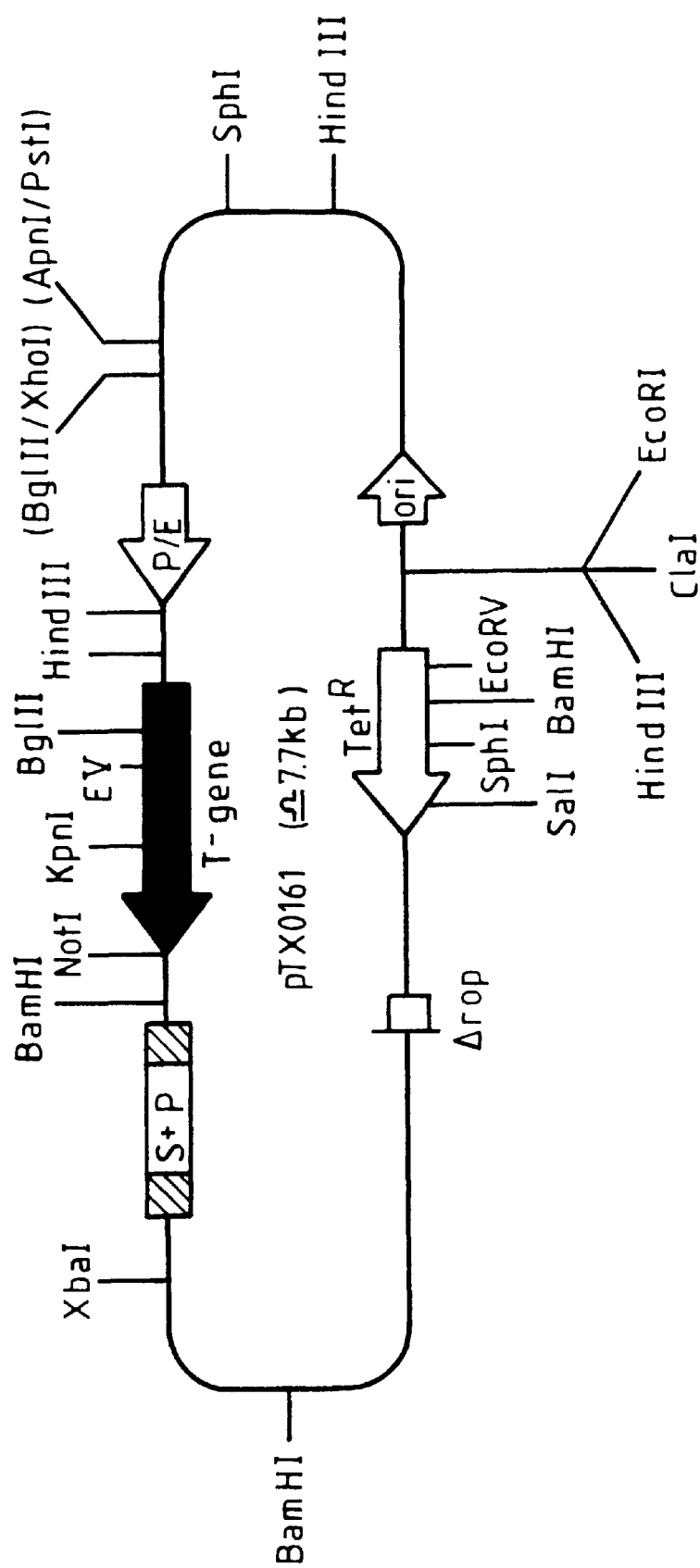
FIG. 13 is a plasmid map of pTX0161.
Figure 14:
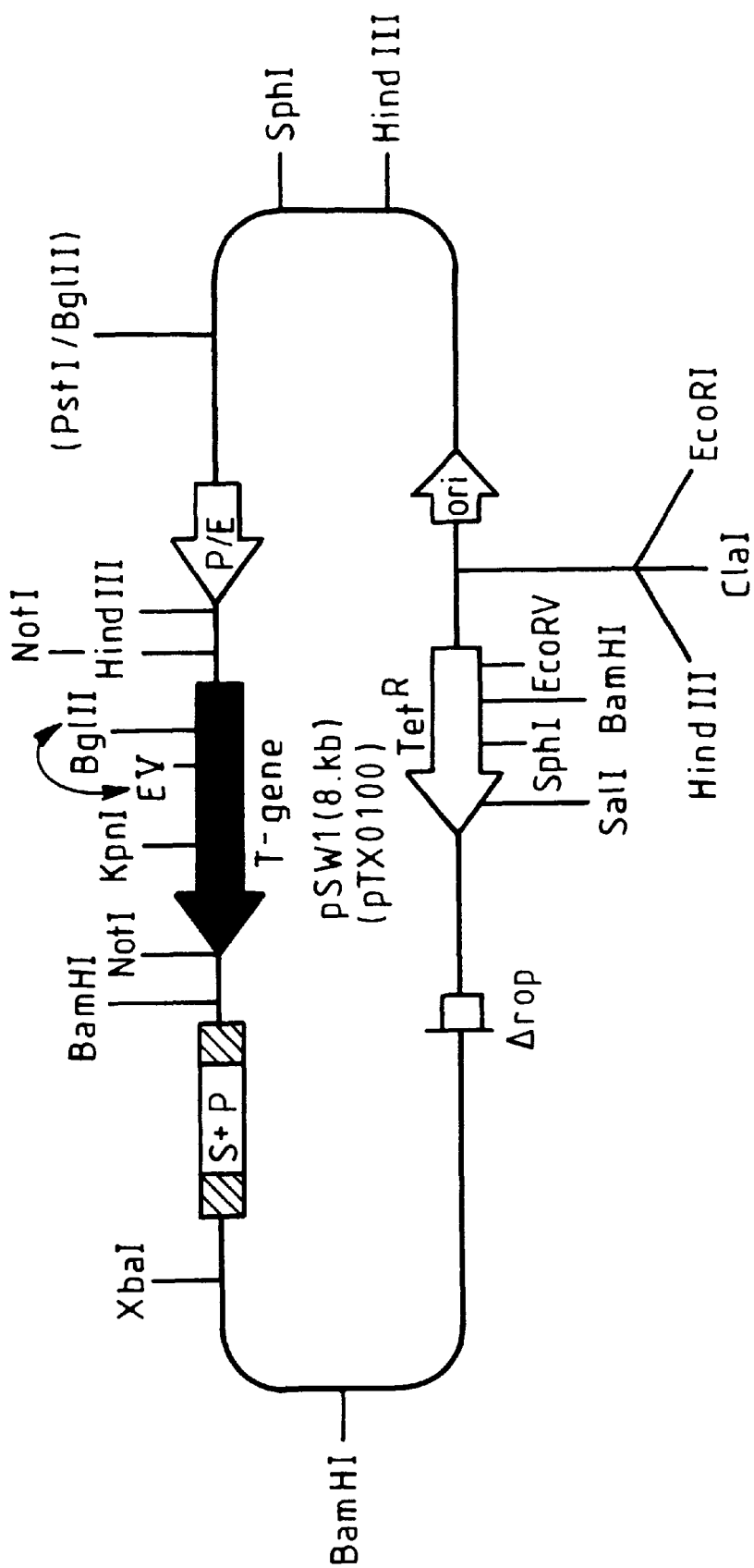
FIG. 14 is a plasmid map of pTX0100.
Figure 15:
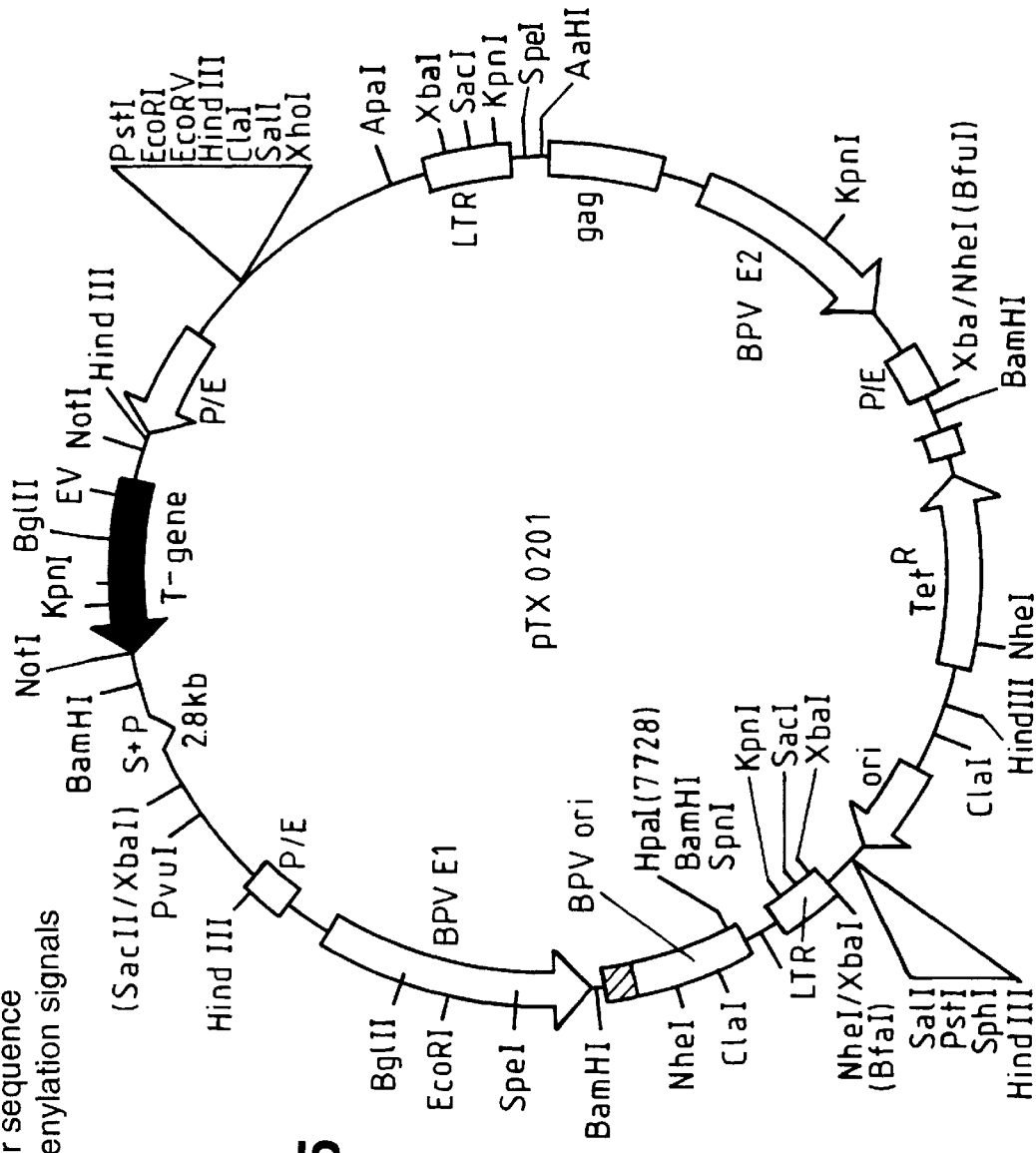
FIG. 15 is a plasmid map of pTX0201.

FIG. 11 shows a 0.8% agarose gel of the plasmid recovered from the three samples. 500 ng of each of the three samples was loaded at 0.5 mg level. Lane 1 is a 1 kb size marker. In Lane 2 is a caesium chloride purified preparation. In Lanes 3, 4 and 5 are 0.15, 0.175 and 0.2M NaOH in 1% SDS samples respectively. Note in Lane 5, the 0.2M NaOH lysis buffer treated sample, the presence of an increased mobility irreversibly denatured species is present at 1–5%. Also note in the table above that the yields from this sample are considerably diminished compared to the ther NaOH concentrations at cell lysis, indicating that much of the plasmid has not been recovered and is irretrievable under these conditions. That which has renatured has the increased mobility irreversibly denatured species present.

FIG. 11 shows differences in yield of plasmid DNA.

| Lane No | Sample |
|---|---|
| 1 | 1 Kb marker |
| 2 | Caesium standard pSW1 |
| 3 | 0.15M NaOH lysis buffer sample |
| 4 | 0.175M NaOH lysis buffer sample |
| 5 | 0.20M NaOH lysis buffer sample |

Conclusion

For this plasmid/host strain combination there are differences in both the overall plasmid recovered and quality of the plasmid that was recovered when the concentration of sodium hydroxide was varied in comparable samples. Use of the higher concentration of sodium hydroxide at cell lysis (in this case 0.117M) can result in very high losses in plasmid DNA yield as well as poor quality plasmid DNA (i.e. the presence of irreversibly denatured species). Using the criteria described in the invention, the sodium hydroxide concentration in the lysis buffer for this plasma and host strain combination was again identified as 0.17M to 0.185M as shown

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

We claim:

1. A method for isolation and purification of plasmid DNA, comprising the steps of:
    a) determining the irreversible alkaline denaturation value of said plasmid DNA;
    b) growing a culture of bacterial host cells to a cell density within the range of about 2 g to about 200 g per liter dry weight units, wherein said host cells contain plasmid DNA having an irreversible alkaline denaturation value;
    c) lysing said bacterial cells by contacting said culture during exponential growth with an amount of alkali sufficient to reach a pH value that is about 0.1 pH unit to about 0.2 pH unit below the irreversible alkaline denaturation value of said plasmid DNA; and d) isolating a said plasmid DNA preparation.

2. The method of claim 1 wherein the pH of said lysing step is about 0.2 pH units below said irreversible alkaline denaturation value.

3. A method for determining the optimum lysis conditions for lysing host cells containing plasmid DNA, comprising the steps of:

a) growing a culture of bacterial host cells to a cell density within the range of about 2 g to about 200 g per liter dry weight units;

b) lysing said bacterial cells during exponential growth at a pH of said culture sufficient to cause cell lysis and to cause denaturation of no greater than 50% of plasmid DNA contained in said cells; and c) selecting a pH value for optimum lysis conditions which is about 0.1 pH units below said pH of step b).

4. The method of claim 3 wherein said lysing step b) is performed at a pH sufficient to cause denaturation of no greater than 90–95% of plasmid DNA, and the pH selected in said step c) is about 0.17–2.0 pH units below said step b) pH.

5. The method of claim 1 or claim 3, wherein said growing step comprises batch fermentation.

6. The method of claim 5 wherein said batch fermentation includes fermentation medium containing glycerol as a carbon source.

7. The method of claim 1 or claim 3, wherein said growing step includes the step of controlling the feed rate of a carbon source.

8. The method of claim 7 wherein said growing step comprises fed-batch fermentation.

9. The method of claim 8 wherein said fed-batch fermentation includes a fermentation medium containing one of glycerol or glucose as a carbon source.

10. The method of claim 1 or 3 wherein said growing step comprises culturing said cells in a fermentation medium comprising excess nucleic acid precursors and vitamins.

11. The method of claim 10 wherein said fermentation medium comprises about 20 gm/liter yeast extract.

12. The method of claim 11 wherein said fermentation medium comprises 5 gm/liter of an ammonium salt.

13. The method of claim 12 wherein said fermentation medium comprises 10 gm/liter of an ammonium salt.

14. The method of claim 12 wherein said ammonium salt is ammonium sulfate, ammonium nitrate, or ammonium phosphate.

15. The method of claim 1 or 3 wherein said pH value is in the range of approximately 12.1 to 12.9.

16. The method of claim 1 or 3 wherein said plasmid DNA is in the range of approximately 5 kb to approximately 50 kb.

17. The method of claim 16 wherein said plasmid DNA comprises mammalian DNA is in the range of approximately 5 kb to 50 kb.

18. The method of claim 1 wherein said plasmid DNA preparation is isolated in a pharmaceutically acceptable solution.

19. The method of claim 1, said lysis step (c) being performed at between about 10 to about 60 g/l dry weight of cells.

20. The method of claim 1 wherein said isolating step (d) comprises ion exchange chromatography including the step of fluidized bed ion exchange chromatography.

21. The method of claim 20 wherein said ion exchange chromatography further comprises axial or radial high resolution anion exchange chromatography.

22. The method of claim 1 wherein said isolating step (d) including fluidized bed ion exchange chromatography.

23. The method of claim 22 wherein said isolating step (d) including gel permeation chromatography.

24. The method of claim 21 said isolation step (d) further comprising, after said high resolution anion exchange chromatography, gel permeation chromatography.

25. The method of claim 1 wherein said lysing step comprises the steps of:

a) adjusting the pH of said bacterial cells to approximately 12.0; and b) further adjusting the pH of said bacterial cells to a pH value that is between approximately 12.1 and approximately 12.9.

26. The method of claim 25 wherein said further adjusting step b) comprises adding an amount of sodium hydroxide to said culture that is in the range of 0.1–0.2M.

27. The method of claim 1 wherein said lysing step comprises the step of:

a) obtaining a sample aliquot of said culture;

b) determining the irreversible alkaline denaturation value of said plasmid DNA; and c) adjusting the pH of said bacterial cells to 0.1–0.2 pH units below said irreversible alkaline denaturation value.

28. The method of claim 1 wherein in said step (b) the volume of said culture is 50 liters.

29. The method of claim 28 wherein said volume is 500 liters.

30. The method of claim 1 wherein in said step (a) the volume of said culture is greater than 500 L.

31. The method of claim 1 wherein said preparation of plasmid DNA obtained from said isolating step (d) comprises less than about 5% chromosomal DNA.

32. The method of claim 31 wherein said preparation of plasmid DNA obtained from said isolating step (d) comprises less than about 1% chromosomal DNA.

33. The method of claim 1 wherein said preparation of plasmid DNA obtained from said isolating step (d) comprises less than about 100 Eu/mg endotoxin.

34. The method of claim 1 wherein said preparation of plasmid DNA obtained from said isolating step (d) comprises less than about 1% protein.

35. The method of claim 1 wherein said preparation of plasmid DNA obtained from said isolating step (d) comprises less than about 0.2% RNA.

36. The method of claim 1 wherein greater than about 90% of said preparation of plasmid DNA obtained from said isolating step (c) is in circular form.

* * * * *